US012594006B2

(12) United States Patent
  Ionescu Stoll et al.

(10) Patent No.:    US 12,594,006 B2
(45) Date of Patent:       Apr. 7, 2026

(54) SMARTPHONE APPLICATION WITH POP-OPEN SOUNDWAVE GUIDE FOR DIAGNOSING OTITIS MEDIA IN A TELEMEDICINE ENVIRONMENT

(71) Applicant: Wavely Diagnostic Inc., Seattle, WA (US)

(72) Inventors: Arna Ionescu Stoll, Seattle, WA (US); Thomas Edwards, Seattle, WA (US); Treasure Lynae Hinds, Issaquah, WA (US); Gregory Thomas Janky, Sammamish, WA (US)

(73) Assignee: Wavely Diagnostic Inc., Seattle, WA (US)

( * ) Notice: Subject to any disclaimer, the term of this patent is extended or adjusted under 35 U.S.C. 154(b) by 720 days.

(21) Appl. No.: 17/958,307

(22) Filed: Sep. 30, 2022

(65) Prior Publication Data

US 2023/0103268 A1      Mar. 30, 2023

Related U.S. Application Data

(60) Provisional application No. 63/251,012, filed on Sep. 30, 2021.

(51) Int. Cl.
  *A61B 5/12*    (2006.01)
  *A61B 1/227*    (2006.01)
  *A61B 5/01*    (2006.01)
  *G16H 40/40*    (2018.01)
  *G16H 40/67*    (2018.01)
  *G16H 50/20*    (2018.01)

(52) U.S. Cl.
  CPC .............. *A61B 5/125* (2013.01); *A61B 1/227* (2013.01); *A61B 5/01* (2013.01); *G16H 40/40* (2018.01); *G16H 40/67* (2018.01); *G16H 50/20* (2018.01)

(58) Field of Classification Search
  CPC ........... A61B 5/125; A61B 1/227; A61B 5/01; A61B 5/6817; A61B 5/12; A61B 2560/0443; A61B 5/6898; G16H 40/40; G16H 40/67; G16H 50/20
  See application file for complete search history.

(56) References Cited

U.S. PATENT DOCUMENTS

2010/0290659 A1    11/2010  Tagami et al.
2021/0186426 A1*   6/2021  Raju ..................... H04R 1/345

FOREIGN PATENT DOCUMENTS

EP         1475035 B1    6/2011
EP         2966881 A1    1/2016
WO         8303192 A1    9/1983
WO      2017189944 A1   11/2017

* cited by examiner

*Primary Examiner* — Tse W Chen
*Assistant Examiner* — Evelyn Grace Park
(74) *Attorney, Agent, or Firm* — Jubin Dana; Dana Legal Services

(57)        ABSTRACT

A system and method are disclosed for the remote detection of otitis media in children at home or in other locations for use in a telemedicine environment. The system runs on a smartphone application and is easy for a child's caregiver to use. The system also includes a pop-open soundwave guide that directs an audio signal from a smartphone's speaker to the patient's eardrum and back to the smartphone's microphone.

5 Claims, 18 Drawing Sheets

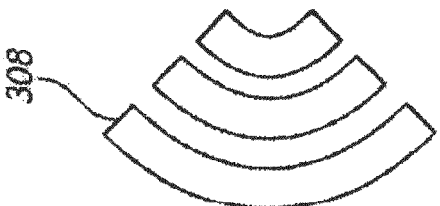
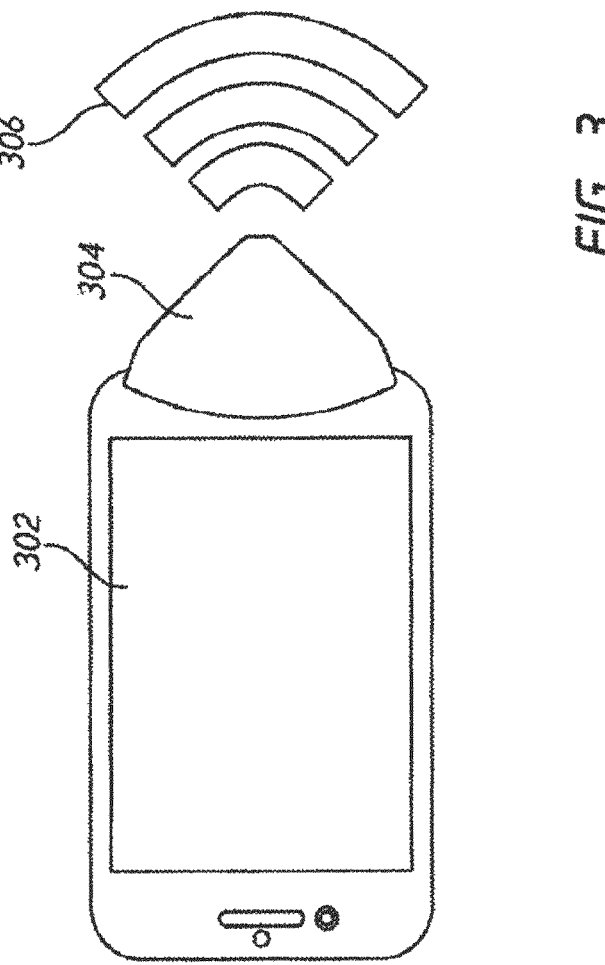
*FIG. 3*

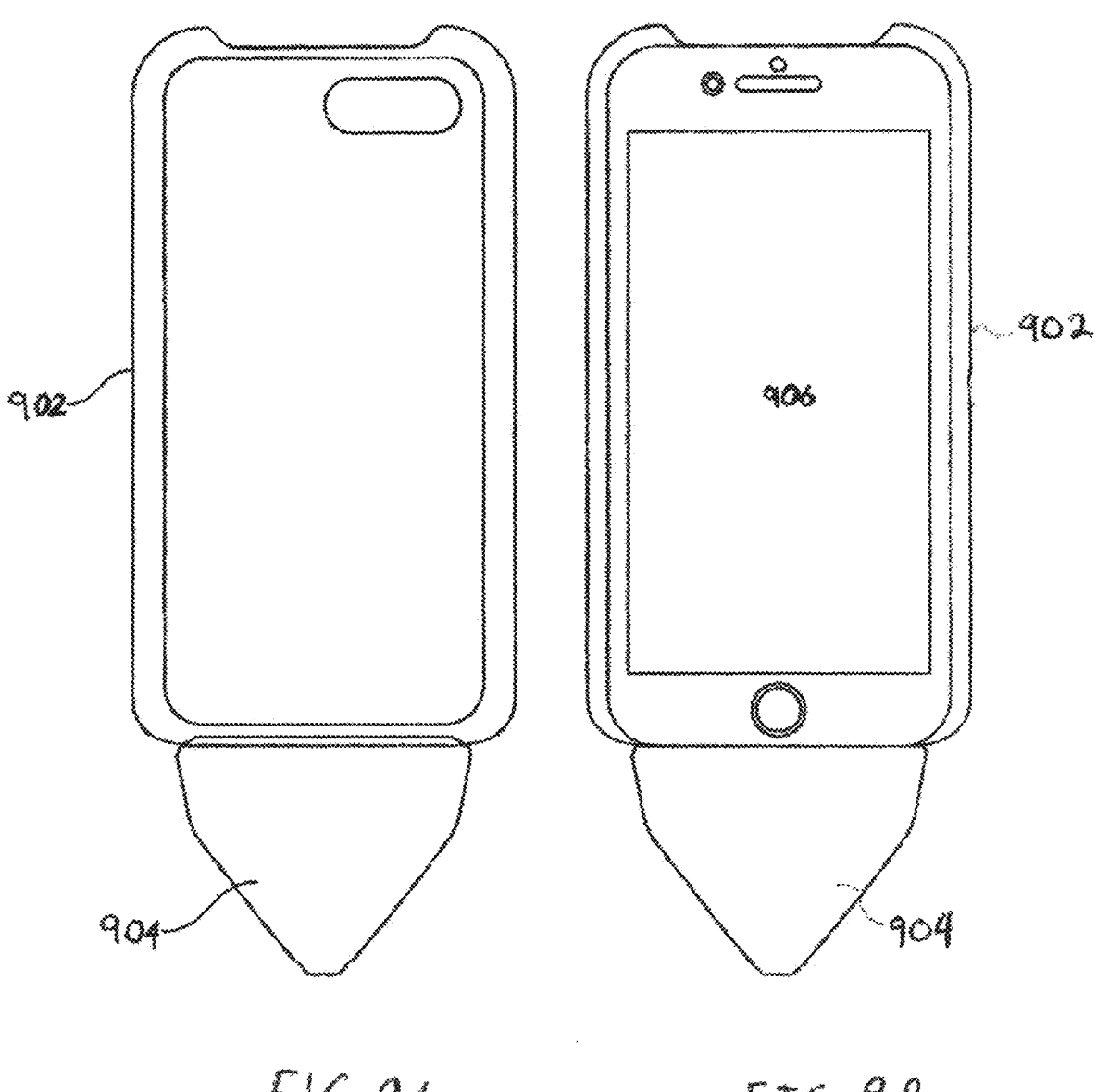
FIG. 9A                    FIG. 9B

1102A

1104

1102 B

1106

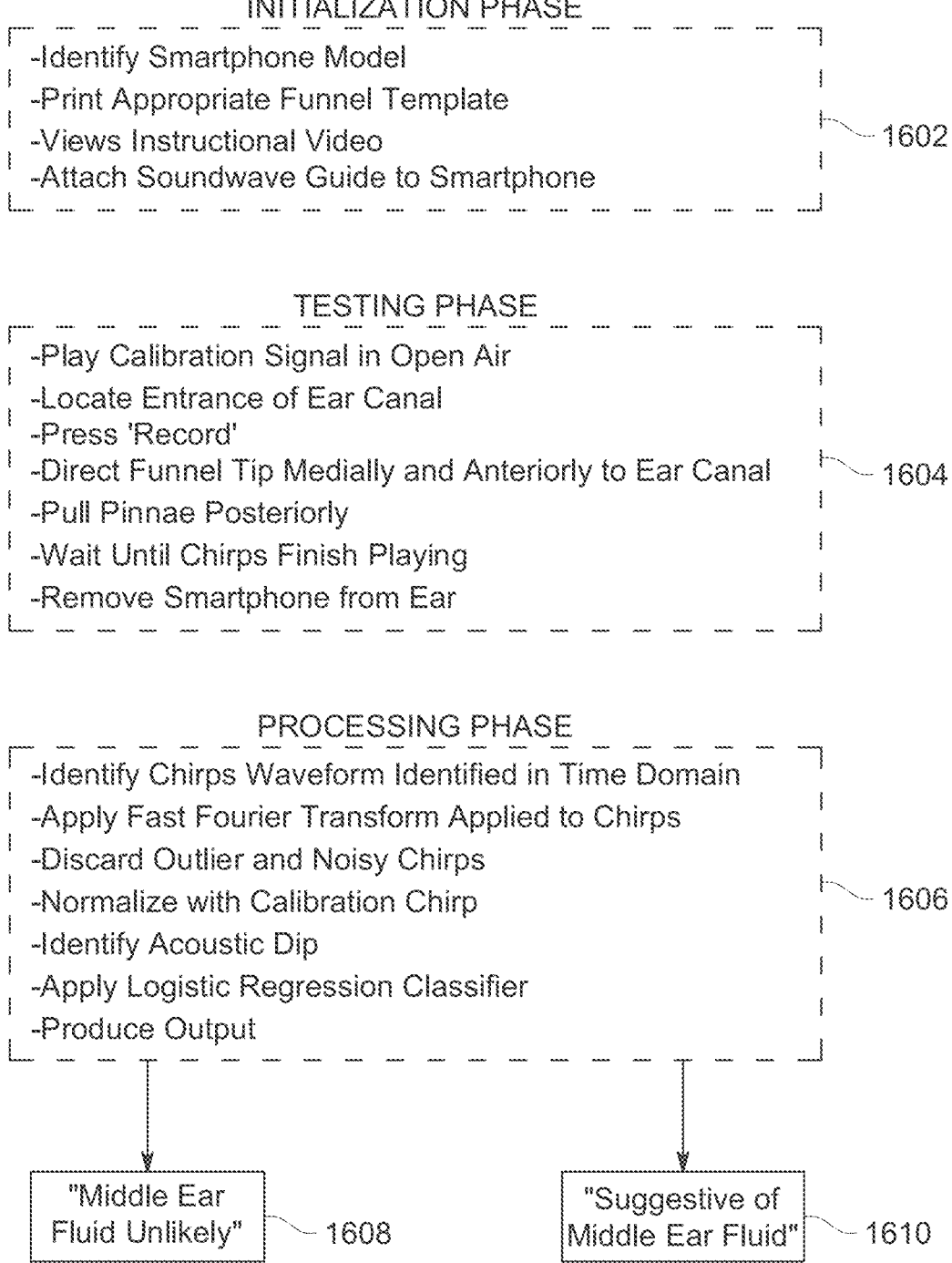

INITIALIZATION PHASE
- Identify Smartphone Model
- Print Appropriate Funnel Template
- Views Instructional Video
- Attach Soundwave Guide to Smartphone

1602

TESTING PHASE
- Play Calibration Signal in Open Air
- Locate Entrance of Ear Canal
- Press 'Record'
- Direct Funnel Tip Medially and Anteriorly to Ear Canal
- Pull Pinnae Posteriorly
- Wait Until Chirps Finish Playing
- Remove Smartphone from Ear

1604

PROCESSING PHASE
- Identify Chirps Waveform Identified in Time Domain
- Apply Fast Fourier Transform Applied to Chirps
- Discard Outlier and Noisy Chirps
- Normalize with Calibration Chirp
- Identify Acoustic Dip
- Apply Logistic Regression Classifier
- Produce Output

1606

"Middle Ear Fluid Unlikely" 1608

"Suggestive of Middle Ear Fluid" 1610

FIG. 16

SMARTPHONE APPLICATION WITH POP-OPEN SOUNDWAVE GUIDE FOR DIAGNOSING OTITIS MEDIA IN A TELEMEDICINE ENVIRONMENT

CROSS REFERENCE TO RELATED APPLICATION

The application claims the priority benefit of U.S. Provisional Application No. 63/251,012 titled SMARTPHONE APPLICATION WITH POP-OPEN SOUNDWAVE GUIDE FOR DIAGNOSING OTITIS MEDIA IN A TELEMEDICINE ENVIRONMENT by Arna IONESCU STOLL and filed on Sep. 30, 2021, the entire disclosure of which is incorporated herein by reference.

TECHNICAL FIELD

The invention is in the field of medical diagnostics devices and, more specifically, related to systems for diagnosing ear conditions at home with the ability to provide feedback to a user based on data analysis.

BACKGROUND

By some measures, the most common reason for a pediatric visit to a health care provider is suspected ear infection (otitis media). There are approximately 30 million such visits in the United States alone each year. These visits are rarely performed at home (virtually) because they require a physical examination of the ear and current virtual examinations require a high-cost device. Few families can afford the high cost of the current technology. Therefore, what is needed is a system and method for providing medical diagnosis of ear conditions at home with the ability to provide feedback to a user based on data analysis.

SUMMARY

In accordance with the various aspects and embodiments of the invention, a system and method are disclosed that provide medical diagnosis of otitis media at home with the ability to provide feedback to a user based on data analysis.

The presence of middle ear fluid is the key diagnostic marker for the two most common pediatric ear diseases acute otitis media (AOM) and otitis media with effusion (OME). AOM, commonly called "ear infection," is characterized by infected fluid in the middle ear. Complications include eardrum perforation, mastoiditis, facial nerve palsy, and meningitis, and leads to 28,000 deaths annually. OME is the presence of middle ear fluid without signs of an acute infection and affects up to 80% of children. OME has few overt symptoms, yet is associated with speech delay, sleep disruption, poor school performance, balance issues, and a higher likelihood of developing AOM. Many of these complications are preventable if middle ear fluid is detected early. Most screening for middle ear fluid is conducted via visual otoscopy, which has an accuracy as low as 51%. Due to these poor detection rates, many patients face delays in treatment, if treated at all. Although more accurate tools like tympanometry, pneumatic otoscopy, otomicroscopy, and invasive myringotomy exist, they require significant expertise and referral to a specialist. Poor diagnostic accuracy leads to overuse of antibiotics. This is accelerating the increase of microbial resistance, a significant societal problem that may cause previously curable diseases to become prominent again.

The various aspects and embodiments of the invention support the 2016 call by the American Academy of Otolaryngology for brief, reliable, and objective methods to detect middle ear fluid as well as new in-home strategies to help parents and caregivers monitor fluid. There is a critical unmet need for an accurate and accessible middle ear fluid screening tool that can be used in resource-limited and domestic settings to prevent misdiagnosis of otitis media.

Currently, the COVID-19 pandemic has led to profound shifts in how medical care is delivered. In place of traditional in-person visits to a health care provider, online telemedicine medical visits have increased dramatically. It is unlikely that medical care will return to pre-pandemic models because patients have discovered the convenience of online virtual medical visits, the technical infrastructure is established, and medical billing pathways now exist.

The invention discloses a system and method using current smartphone technology and a pop-up paper soundwave guide to enable parents at home to conduct accurate and affordable diagnostic tests to detect whether a child has otitis media.

In the past treatment of acute otitis media was usually delayed because of having to schedule an in-person medical visit, waiting a couple of days for the appointment, and finally having their child seen by a health care provider in a clinic. This has traditionally been very painful for a small child with an active ear infection (acute otitis media). In a severe case, the resultant delay could cause damage to the ear.

The instant invention allows a parent or other caregiver at home to perform a highly accurate simple diagnostic test on their suffering child's ear or patient's ear using a smartphone application and a detachable pop open soundwave guide. The test results appear immediately on the smartphone screen and can be transmitted or shown to a health care provider during a telemedicine appointment or can be sent directly to the provider in an urgent situation.

The detachable pop-up paper cone-shaped soundwave guide attaches easily to the smartphone simultaneously covering a speaker and a microphone. In accordance with some aspects and embodiments of the invention, the speaker emits a preprogrammed audio signal, which may include white noise or a specific frequency range, that creates a specific soundwave that travels from the speaker, down the soundwave guide cone and into an ear of a suffering child. The soundwave then bounces off the child's eardrum and returns up the cone-shaped soundwave guide and into the smartphone's microphone. A processor picks up the reflected soundwave, gives it an electronic signature, processes the electronic signature, and uses an algorithm to determine whether there is fluid behind the child's eardrum. If the processor determines there is fluid behind the child's ear it sends a test positive message to the smartphone screen telling the child's caregiver that the test was positive for middle ear fluid and to contact a physician. If the processor determines that there is no fluid behind the child's eardrum it sends a test negative message to the smartphone screen indicating to the child's caregiver that there is no fluid behind the eardrum and no ear infection.

The commercial potential of this invention is tied to use in clinics and telemedicine appointments. Current reimbursement guidelines for this type of diagnostic test are already well established in a clinical setting with the CPT code for acoustic impedance testing.

BRIEF DESCRIPTION OF THE DRAWINGS

In order to understand the invention more fully, a reference is made to the accompanying drawings. The invention is described in accordance with the aspects and embodiments in the following description with reference to the drawings or figures (FIG.), in which like numbers represent the same or similar elements. Understanding that these drawings are not to be considered limitations in the scope of the invention, the presently described aspects and embodiments and the presently understood best mode of the invention are described with additional detail through the use of the accompanying drawings. One skilled in the art will understand that embodiments of the invention may be practiced without various of these particular details.

Figure 1:
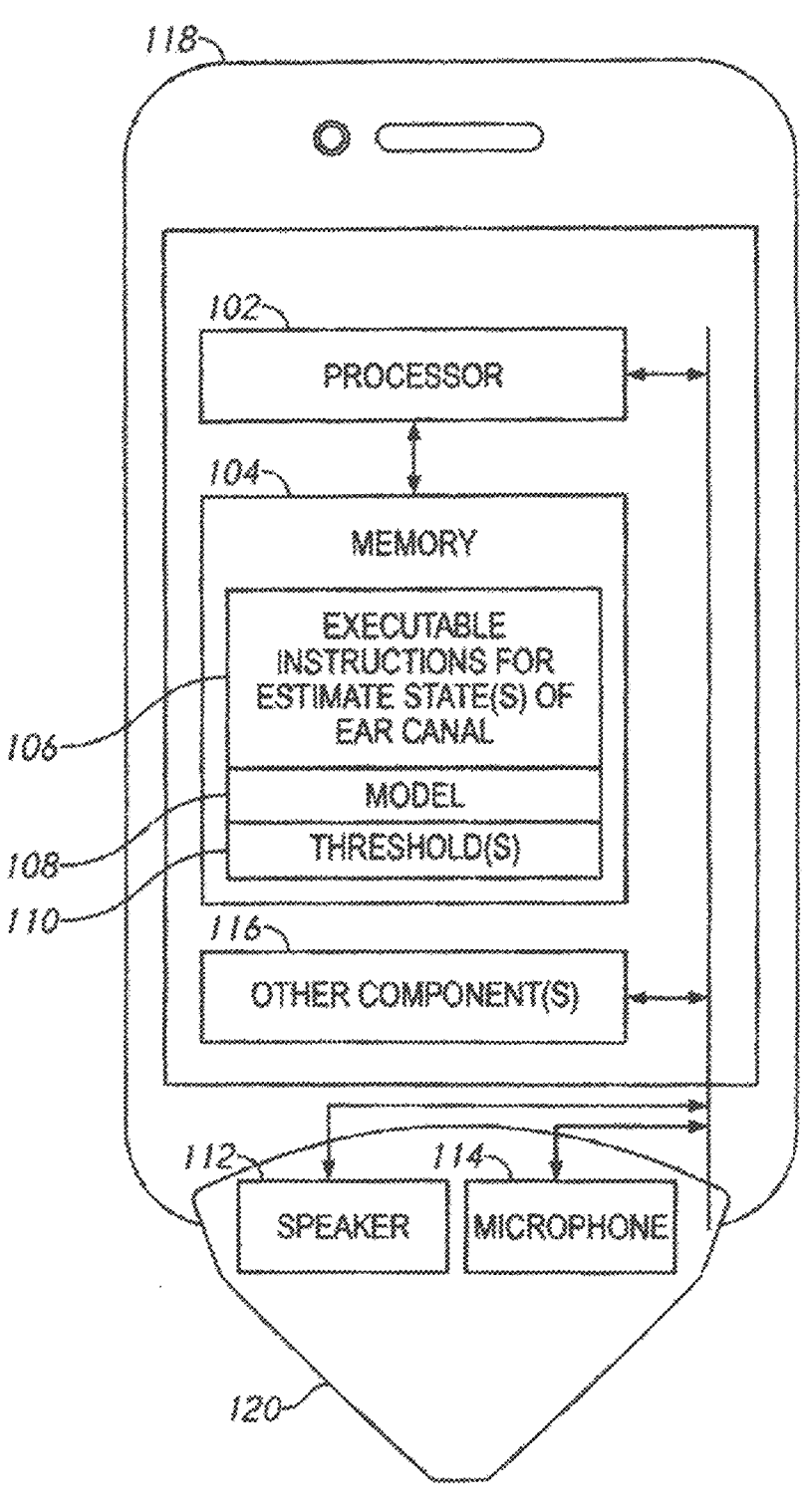

FIG. 1 shows a system arranged in accordance with the various aspects and embodiments of the invention.

Figure 2:
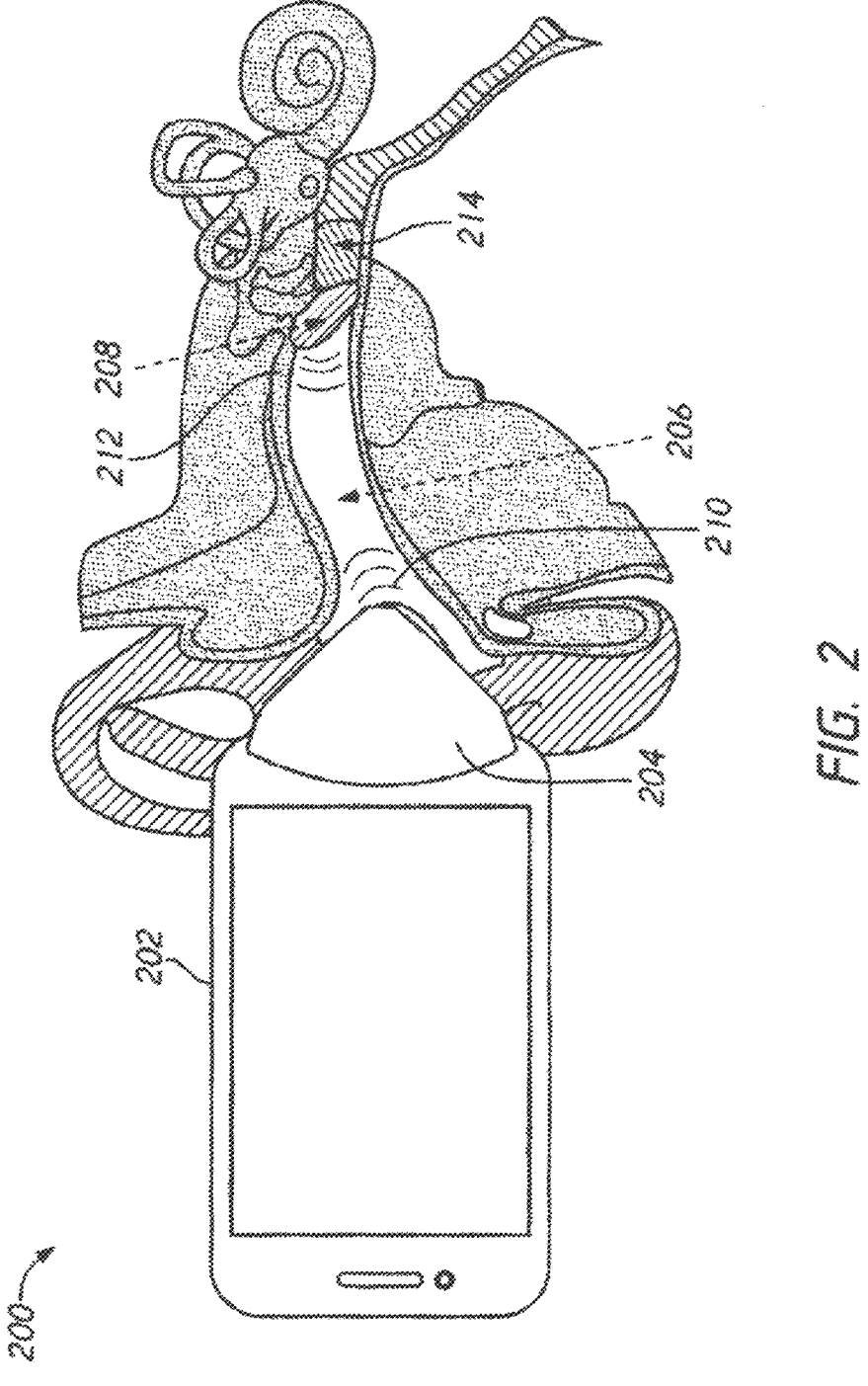

FIG. 2 shows a system engaged in a diagnostic test for AOM/OME in accordance with the various aspects and embodiments of the invention.

FIG. 3 shows a system emitting a diagnostic signal and the resultant reflected signal in accordance with the various aspects and embodiments of the invention.

Figure 4:
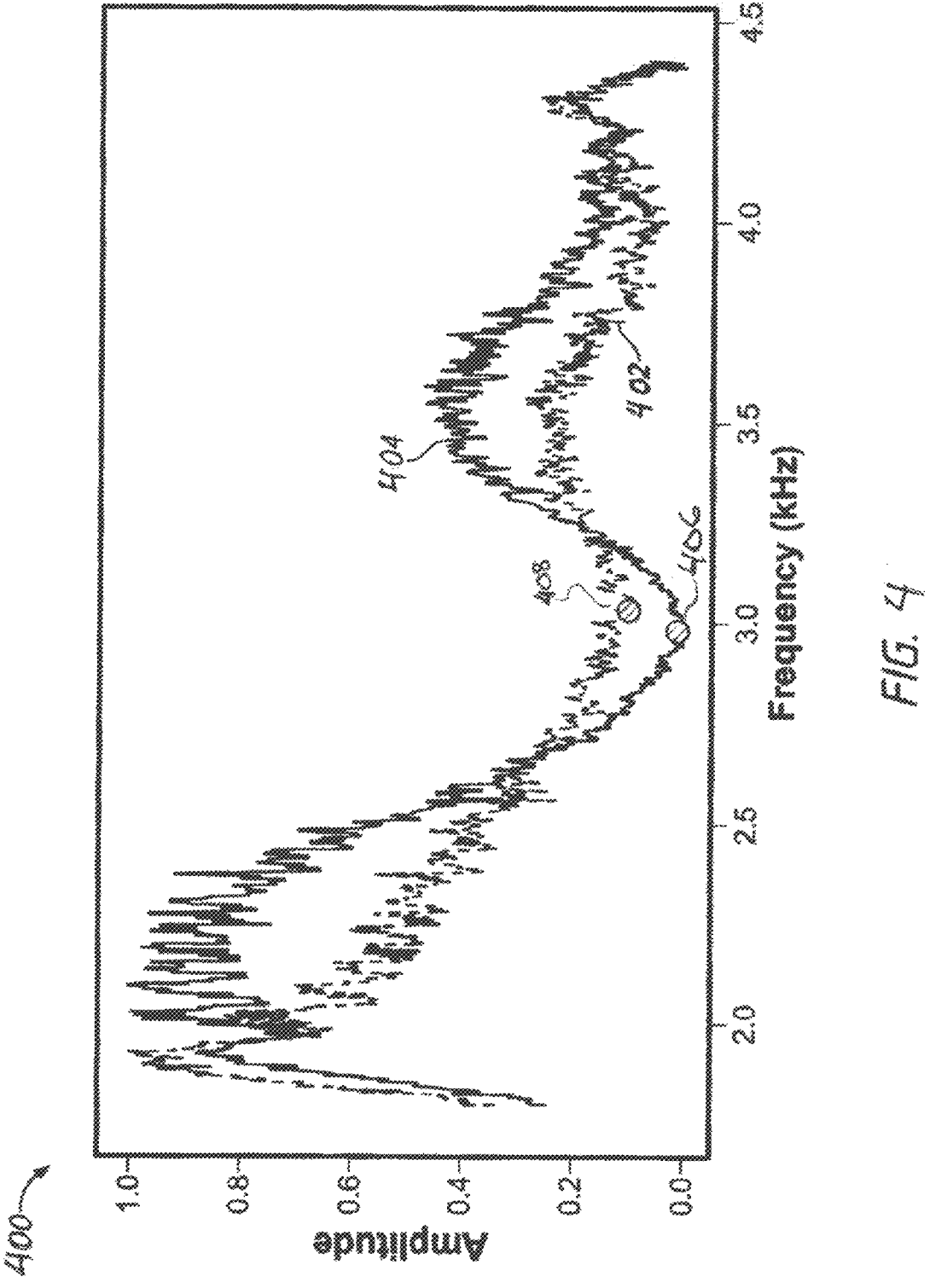

FIG. 4 shows reflected waveforms obtained when an example acoustic signal is played into a patient's ear canal in accordance with the various aspects and embodiments of the invention.

Figure 5:
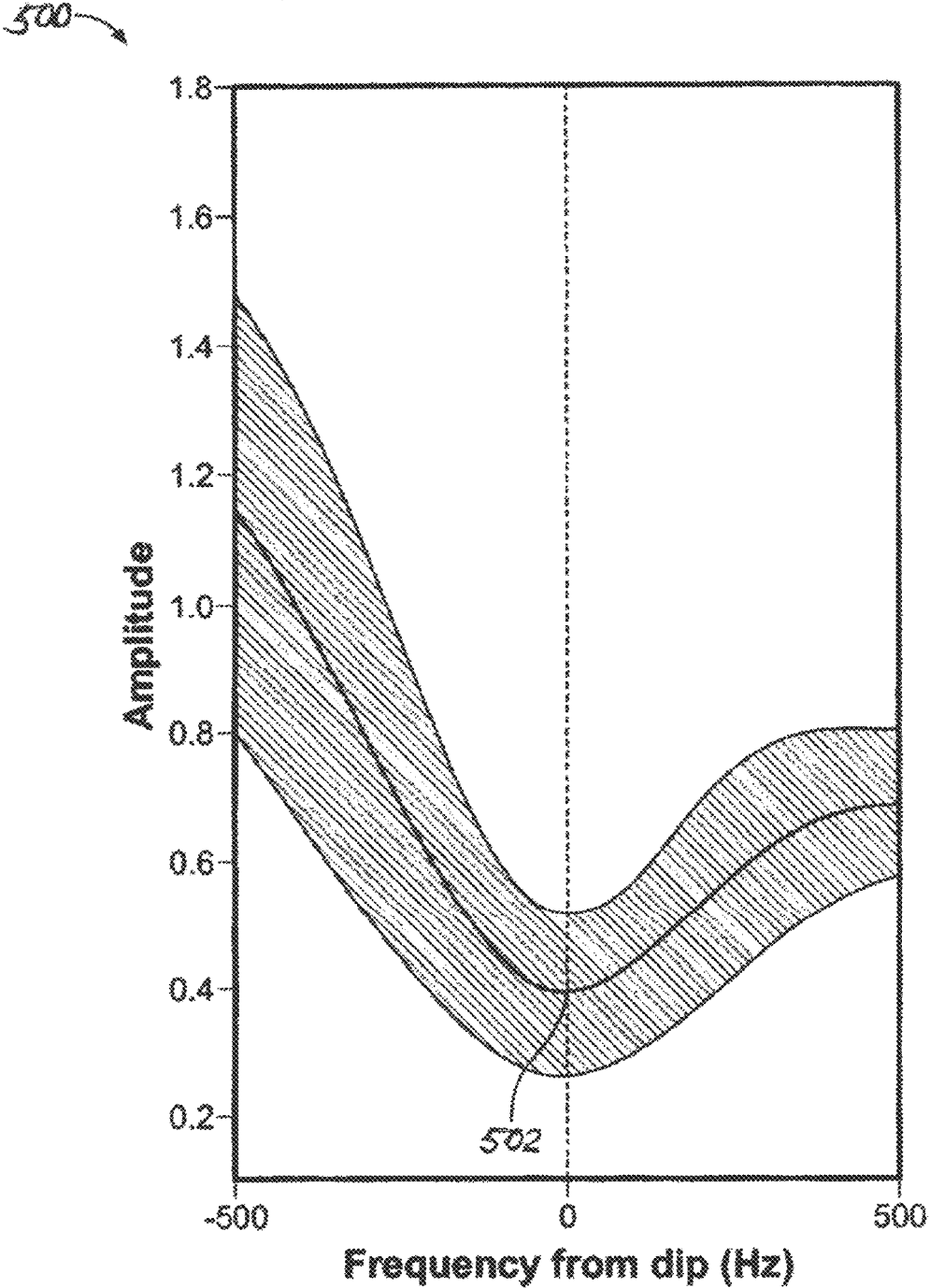

FIG. 5 shows a calibrated acoustic waveform in accordance with the various aspects and embodiments of the invention.

Figures 6A, 6B:
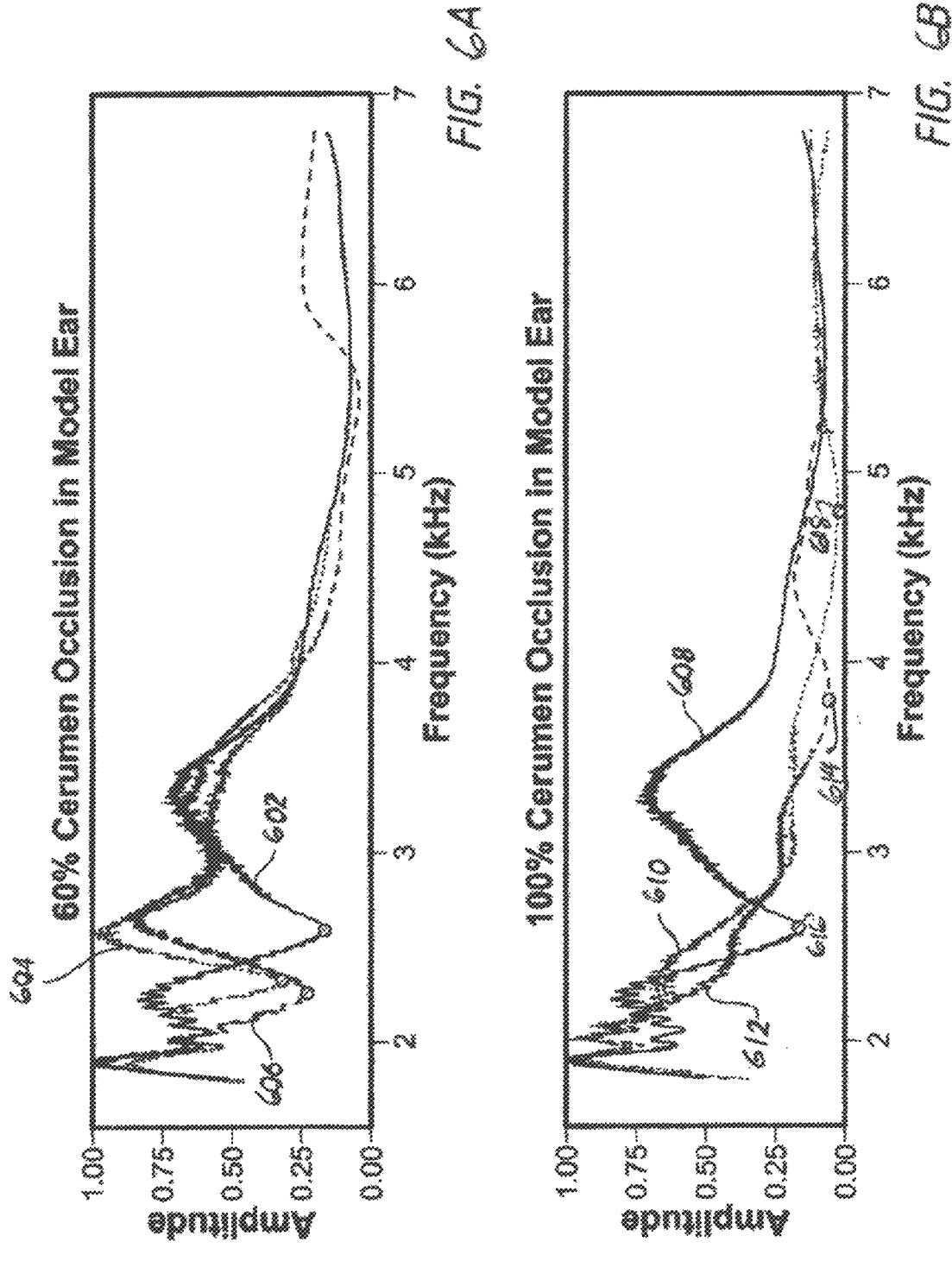
Figure 6C:
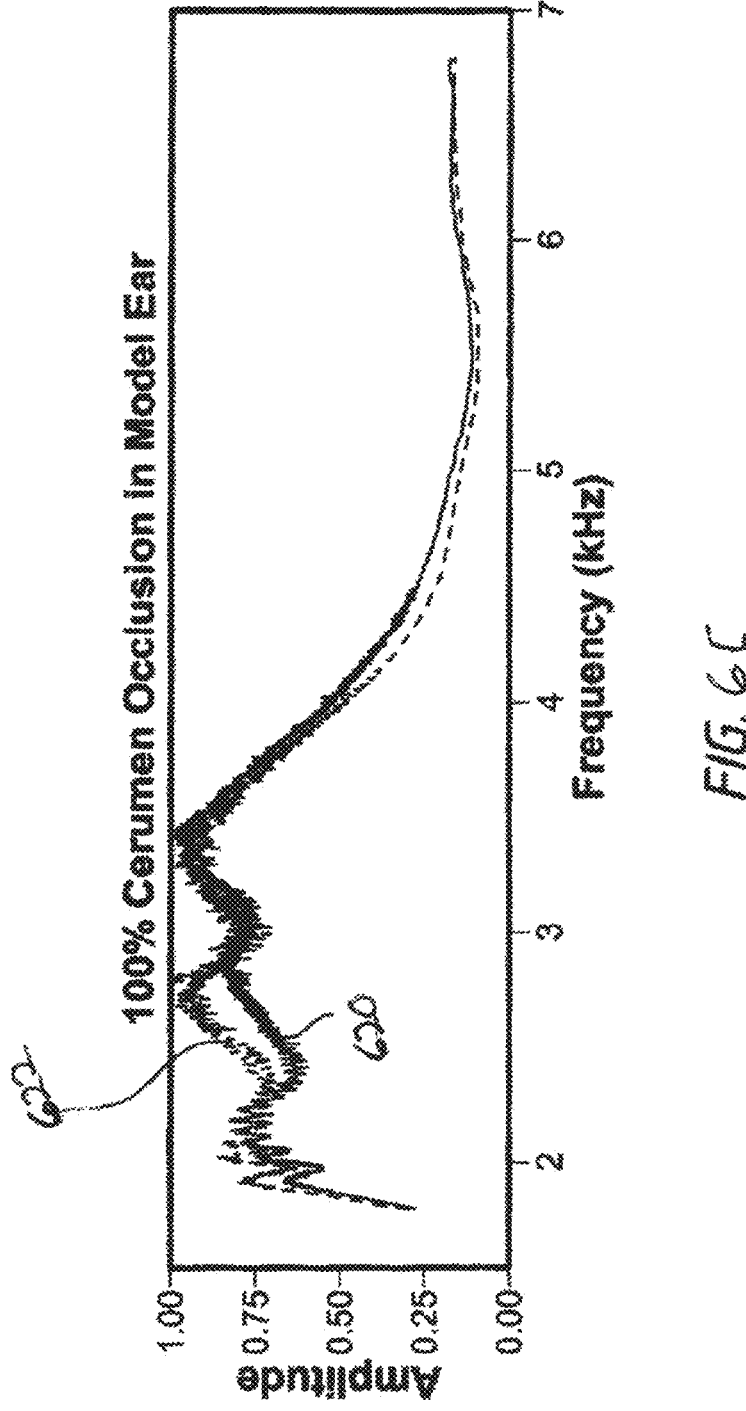

FIG. 6A-FIG. 6C show acoustic waveform for cerumen occlusions in accordance with the various aspects and embodiments of the invention.

Figure 7:
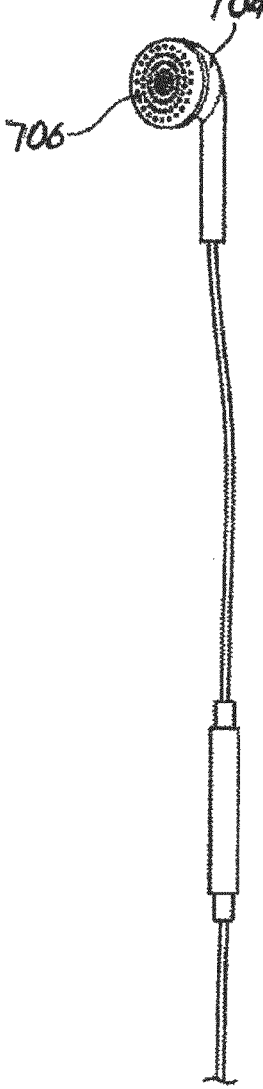

FIG. 7 shows an earpiece apparatus in accordance with the various aspects and embodiments of the invention.

Figures 8A, 8B:
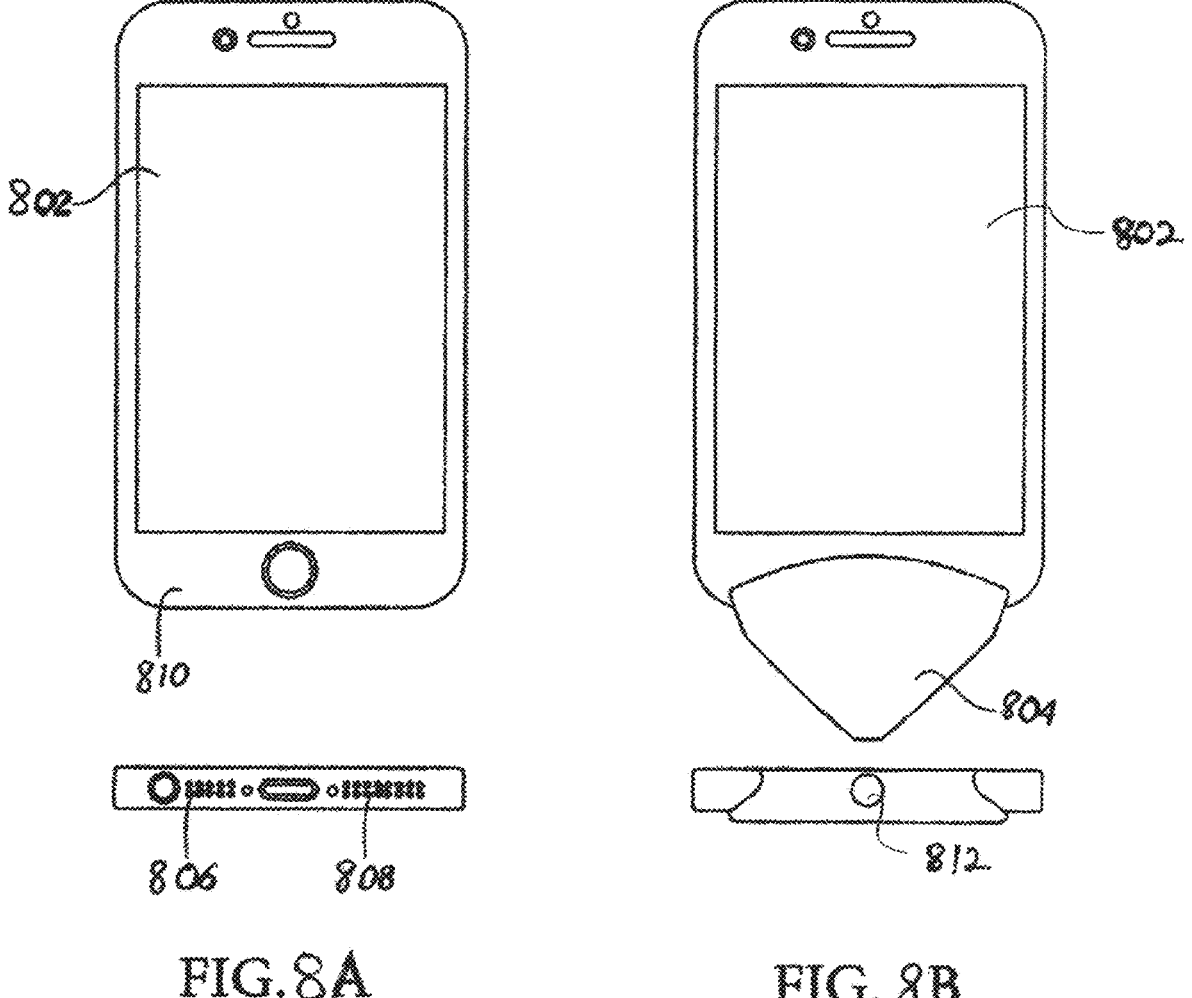

FIG. 8A shows a phone in accordance with the various aspects and embodiments of the invention.

FIG. 8B shows a phone coupled with a soundwave guide in accordance with the various aspects and embodiments of the invention.

FIG. 9 shows a case and a smartphone in accordance with the various aspects and embodiments of the invention.

Figure 10:
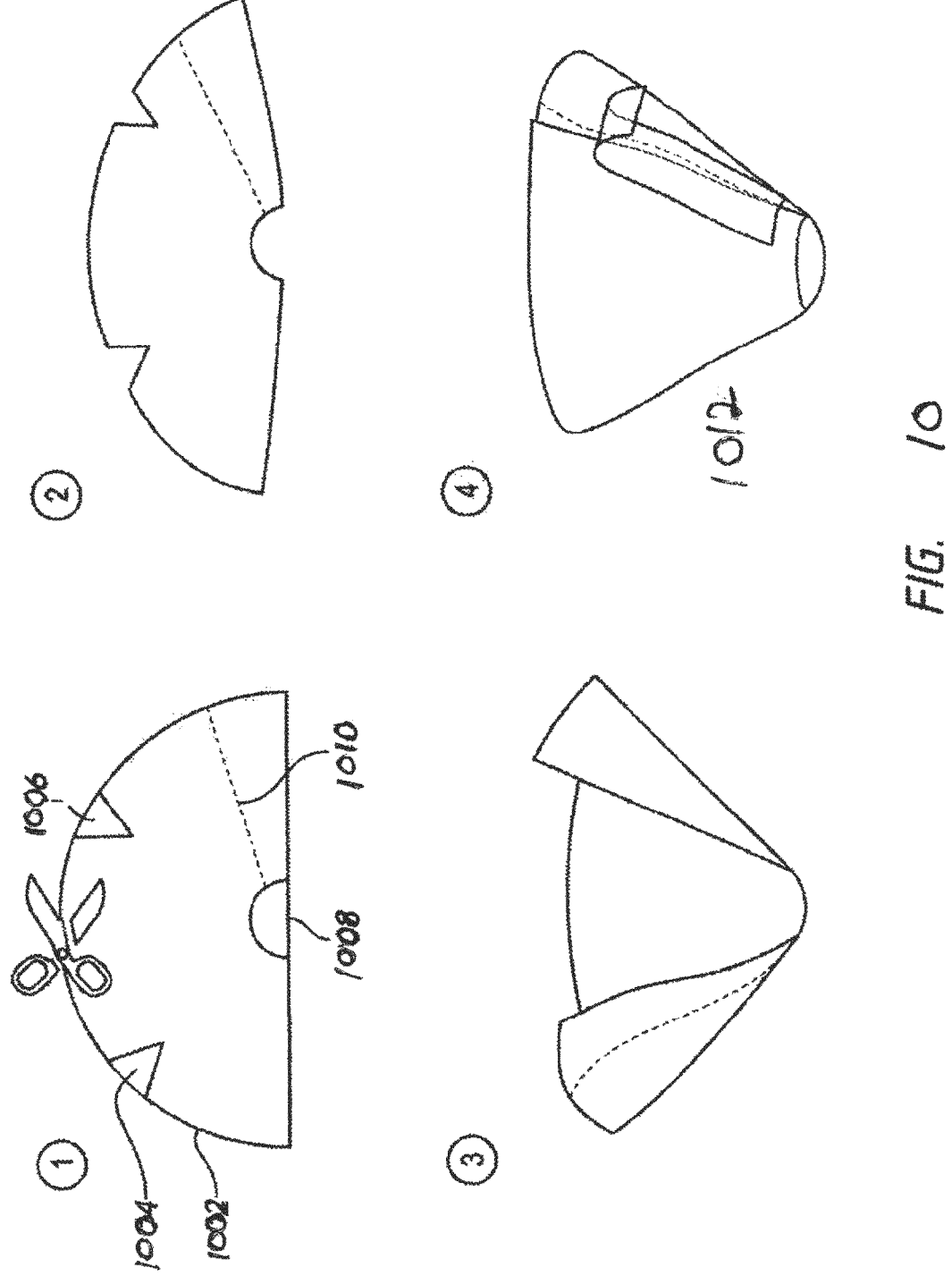

FIG. 10 shows a template for a soundwave guide arranged in accordance with the various aspects and embodiments of the invention.

Figure 11:
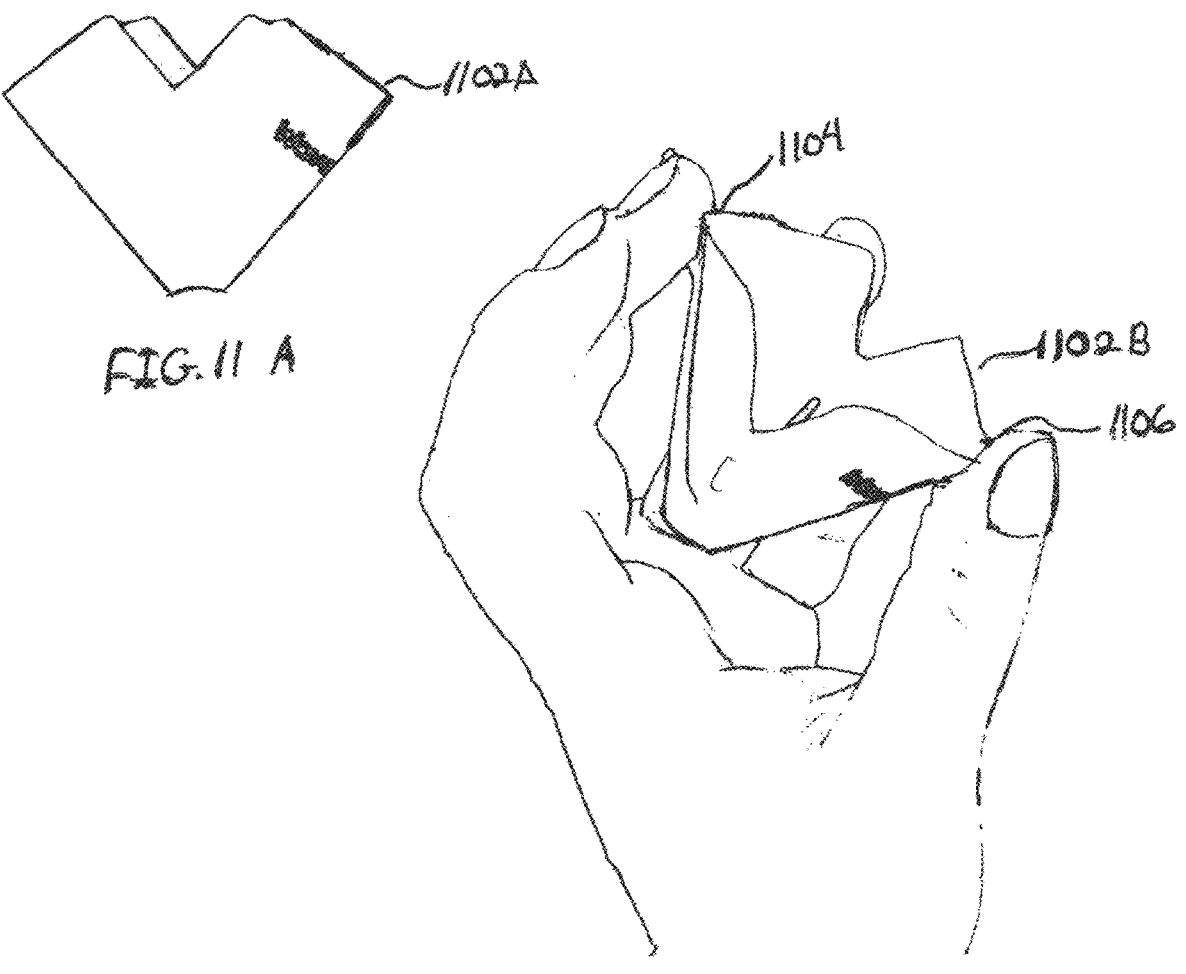

FIG. 11A shows a pop-open soundwave guide in its flat position in accordance with the various aspects and embodiments of the invention.

FIG. 11B shows a pop-open soundwave guide in its popped open position in accordance with the various aspects and embodiments of the invention.

Figure 12:
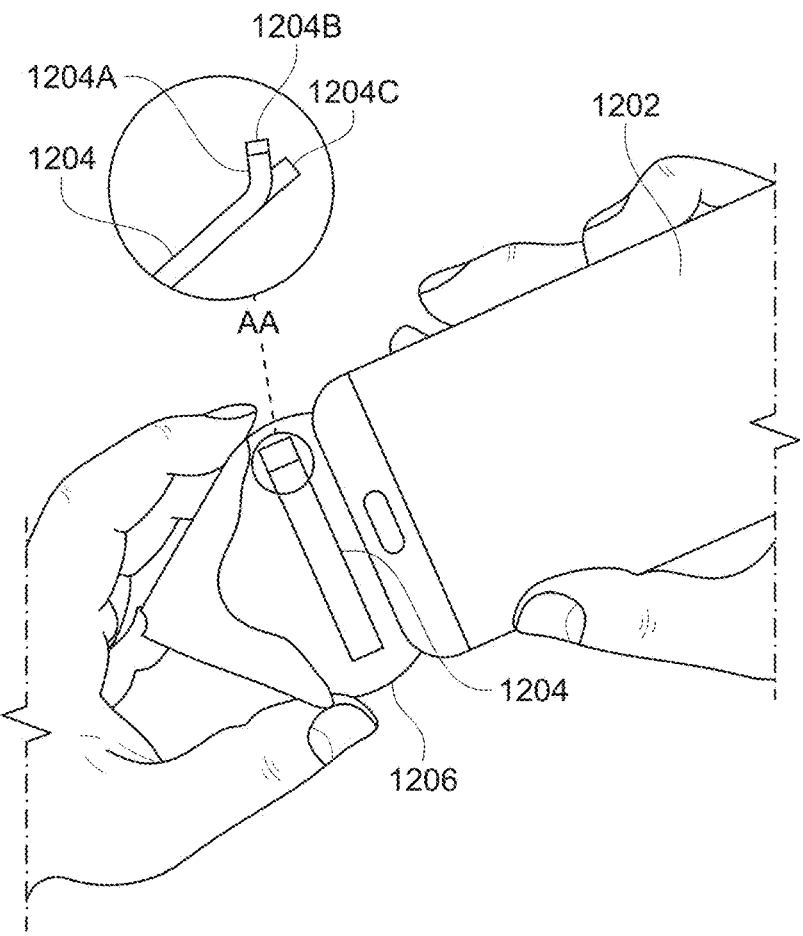

FIG. 12 is a schematic illustration of a pop-open soundwave guide being attached to a smartphone in accordance with the various aspects and embodiments of the invention.

Figure 13:
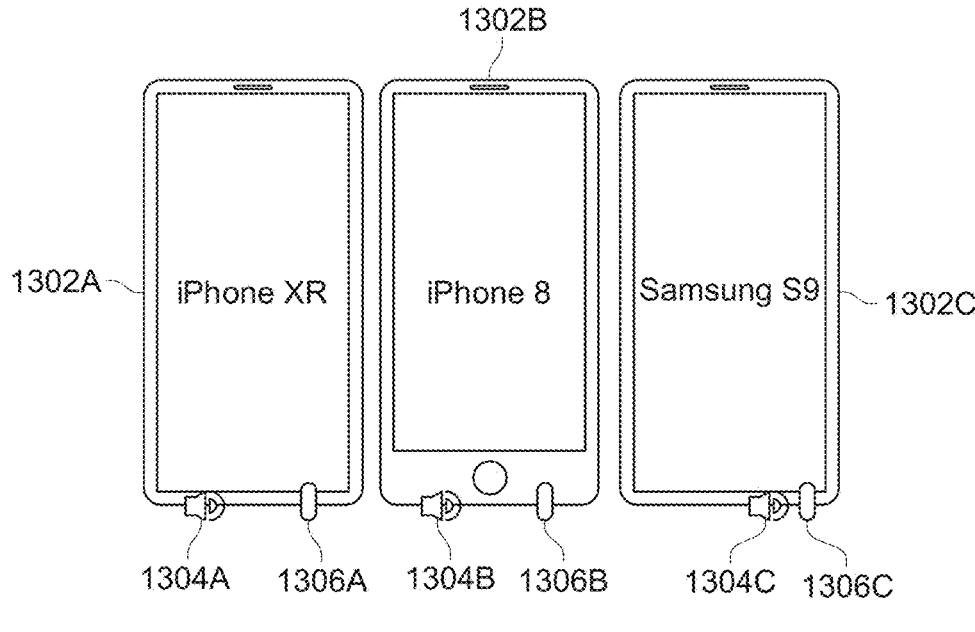

FIG. 13 is a schematic illustration of three smartphone models indicating the relative positions of their respective speakers and microphones.

Figure 14:
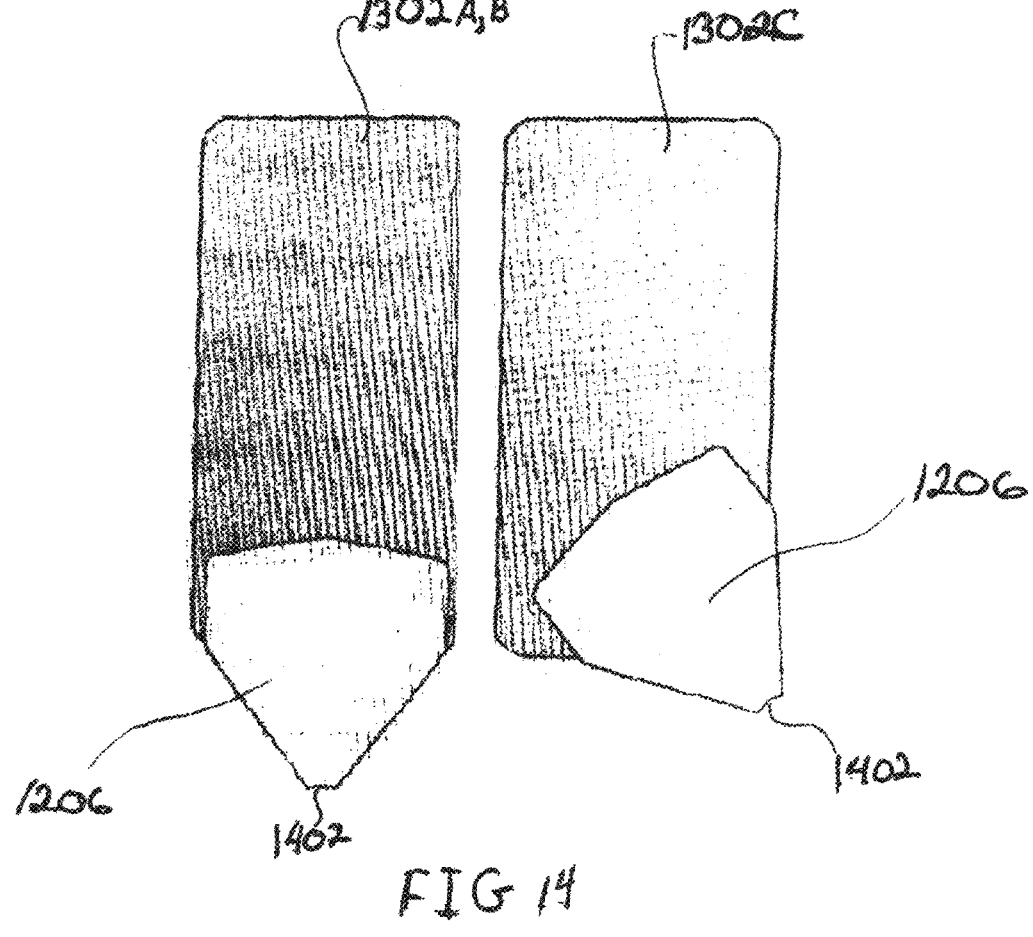
Figure 15:
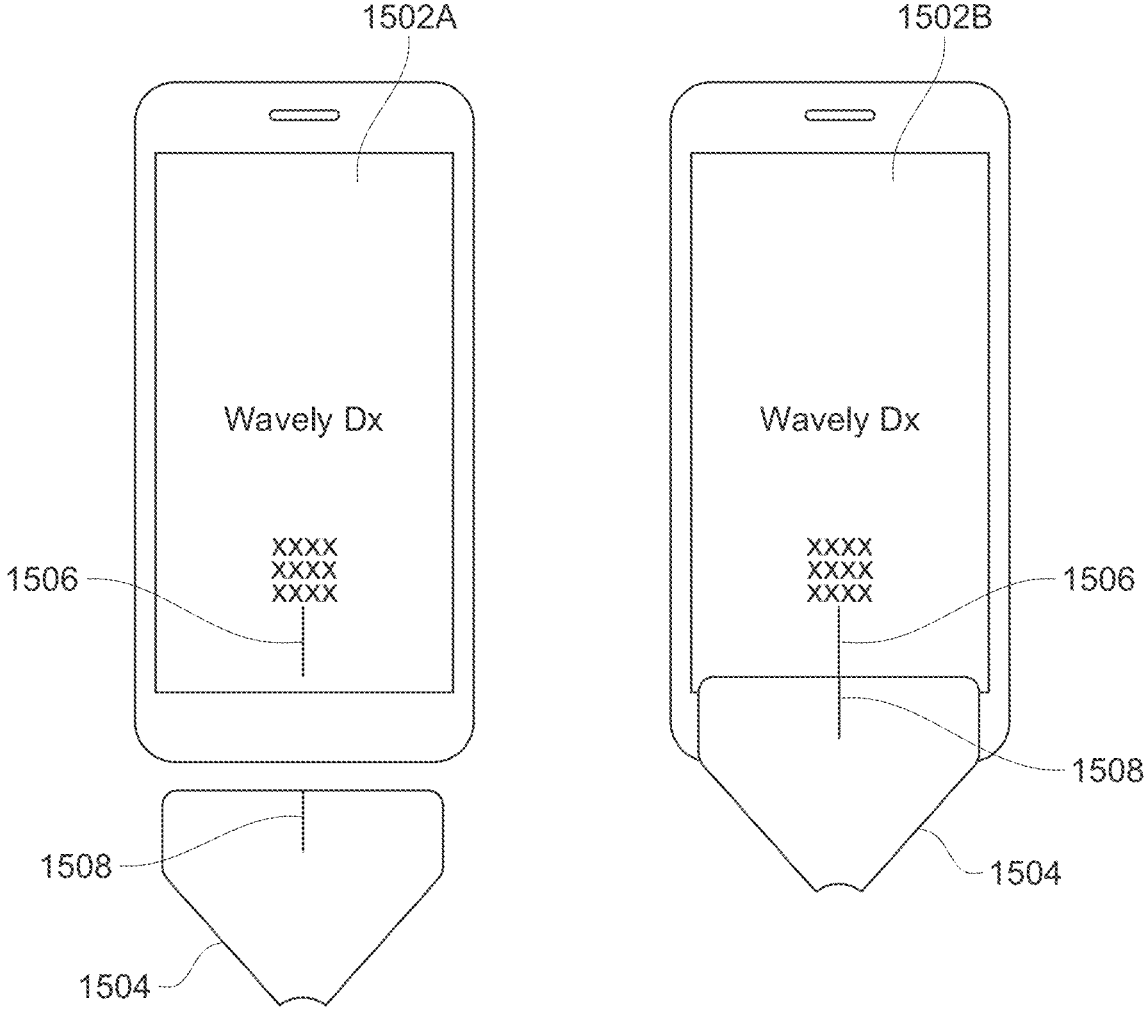
Figure 17A:
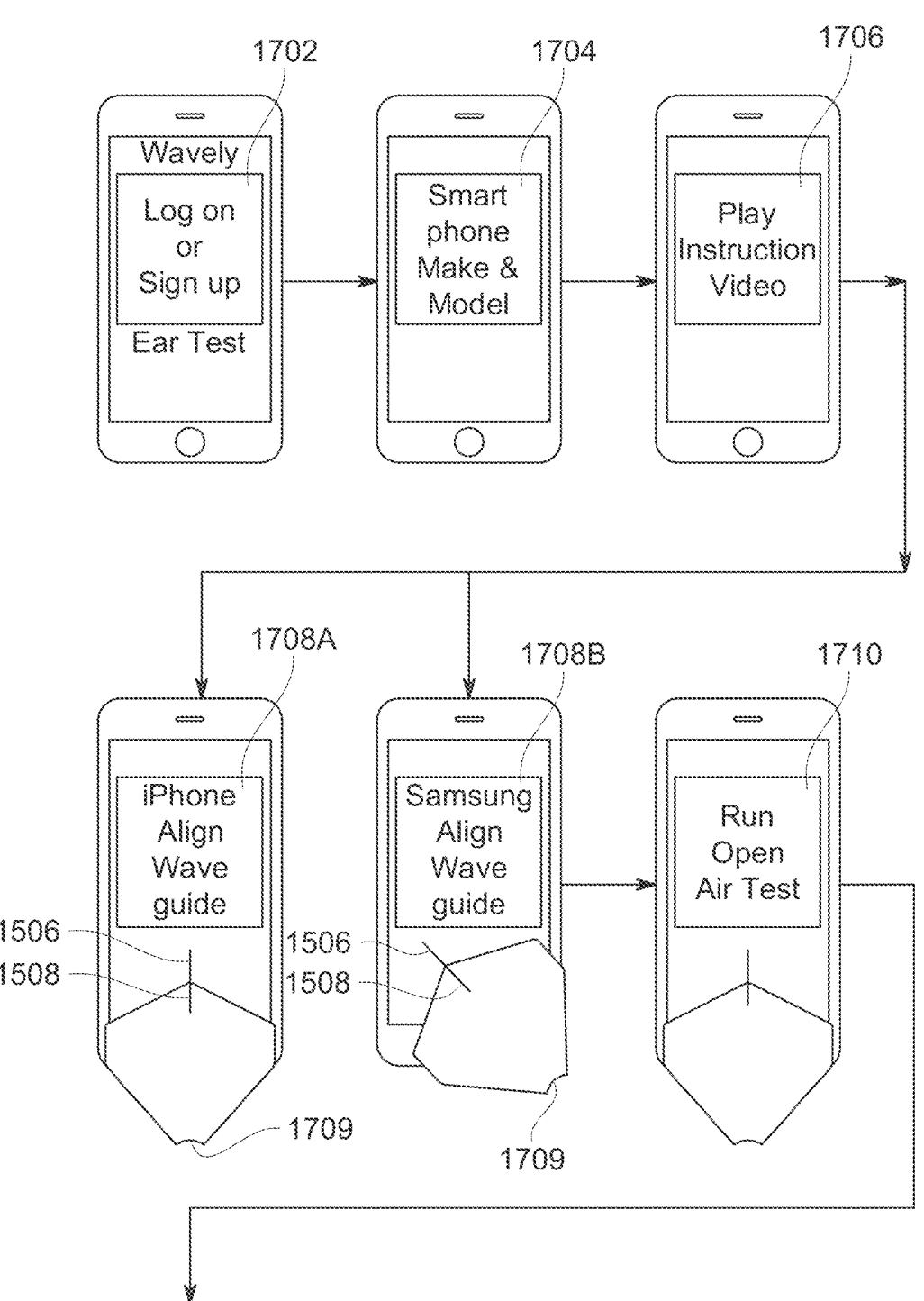
Figure 17B:
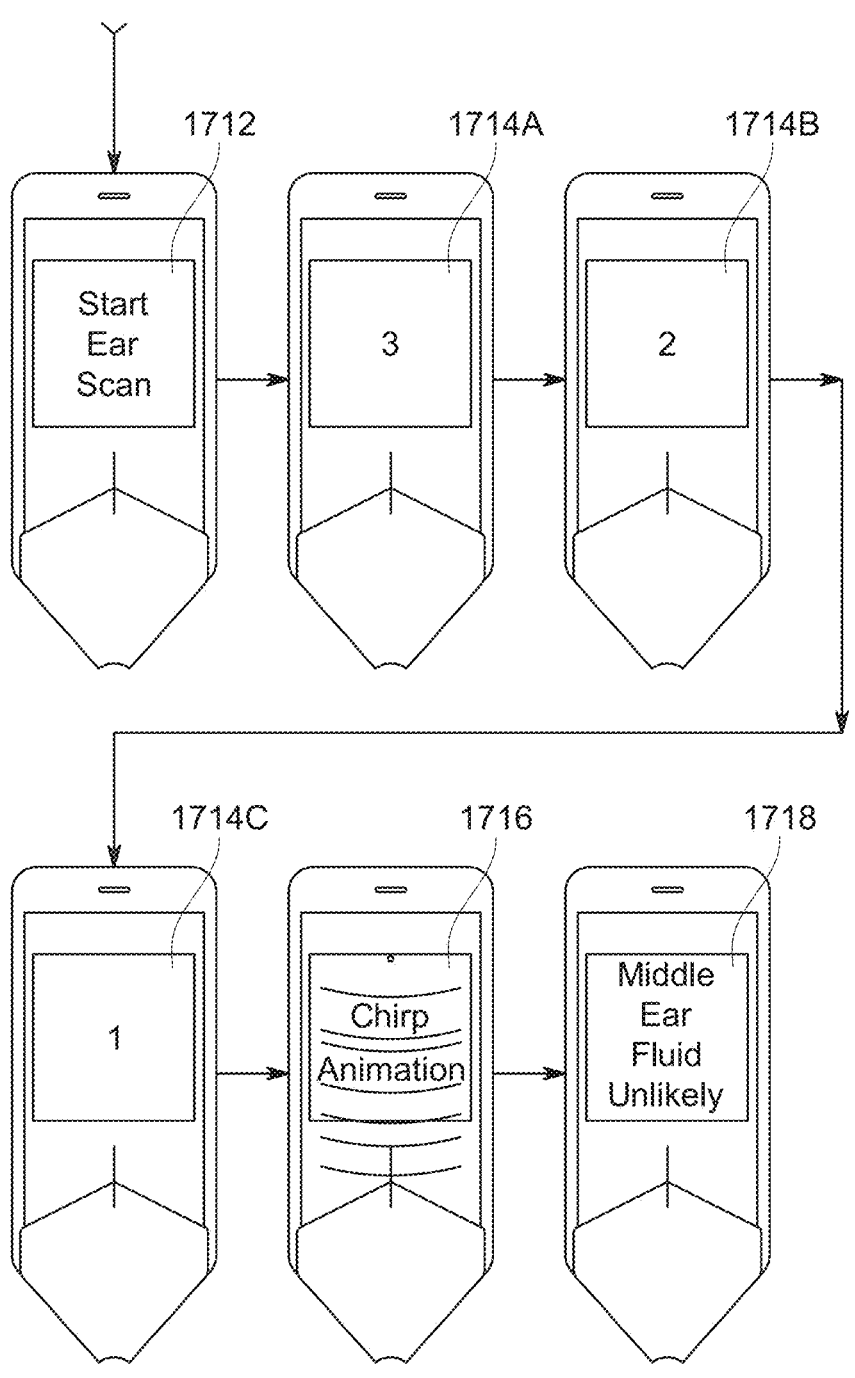

FIG. 14 shows the placement of the pop-open soundwave guide on smartphones with two different speaker/microphone orientations in accordance with the various aspects and embodiments of the invention, FIG. 15 is a schematic illustration of a pop-open soundwave guide being attached to the smartphone using a guide for its proper placement in accordance with the various aspects and embodiments of the invention FIG. 16 is a flowchart illustration of the diagnostic process from initialization to results in accordance with the various aspects and embodiments of the invention, FIG. 17A and FIG. 17B show a diagnostic process executed by an application and displayed on a smartphone's user interface from initial log-on to diagnostic feedback based on test results in accordance with the various aspects and embodiments of the invention.

DETAILED DESCRIPTION

To the extent that the terms "including", "includes," "having", "has", "with", or variants thereof are used in either the detailed description and the claims, such terms are intended to be inclusive in a similar manner to the term "comprising". The invention is described in accordance with the aspects and embodiments in the following description with reference to the figures (FIGs.), in which like numbers represent the same or similar elements.

Reference throughout this specification to "one embodiment," "an embodiment," or "in accordance with some aspects" and similar language means that a particular feature, structure, or characteristic described in connection with the various aspects and embodiments are included in at least one embodiment of the invention. Thus, appearances of the phrases "in accordance with an aspect," "in accordance with one embodiment," "in an embodiment," "in certain embodiments," and similar language throughout this specification refer to the various aspects and embodiments of the invention. It is noted that, as used in this description, the singular forms "a," "an" and "the" include plural referents, unless the context clearly dictates otherwise.

The described features, structures, or characteristics of the invention may be combined in any suitable manner in accordance with the aspects and one or more embodiments of the invention. In the following description, numerous specific details are recited to provide an understanding of various embodiments of the invention. One skilled in the relevant art will recognize, however, that the invention may be practiced without one or more of the specific details, or with other methods, components, materials, and so forth. In other instances, well-known structures, materials, or operations are not shown or described in detail to avoid obscuring the aspects of the invention.

The ranges of values provided herein do not limit the scope of the present invention. It is understood that each intervening value, between the upper and lower limit of that range and any other stated or intervening value in that stated range, is encompassed within the scope of the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Referring now to FIG. 1, according to various aspects and embodiments of the invention shows a graphical illustration of a system for detecting otitis media in a child's ear using a smartphone 118 application and a soundwave guide 120. In the instant invention, the soundwave guide 120 is, but is not limited to, a pop-up paper soundwave guide.

The system of FIG. 1 includes a smartphone 118 and soundwave guide 120. The smartphone 118 includes processor 102, memory 104, other component(s) 116, a speaker 112, and a microphone 114. The memory 104 includes executable instructions for estimate state(s) of an ear canal 106, model 108, and threshold(s) 110. The components shown in FIG. 1 are exemplary. Additional, fewer, and/or different components may be used in other examples.

According to various aspects and embodiments of the invention, a smartphone 118 refers to a computing device. The computing device may be handheld, and may have other uses, such as for cellular phone and/or wireless Internet connectivity, although such other uses may not be utilized or present in some examples. Examples of smartphones include, but are not limited to, tablets or cellular phones, e.g., iPhones, Samsung Galaxy phones, and Google Pixel phones. Smartphones have become widely available and the ability to estimate state(s) of ear canals using smartphones in accordance with techniques described herein may be advantageous in that it may make diagnostics regarding the ear canal more widely available and easily used, particularly during telemedicine appointments occurring in the patients' home.

According to various aspects and embodiments of the invention, the components of the smartphone 118 which may be used in estimating ear canal states (e.g., microphone 114 and/or speaker 112) may not be designed or configured especially for use in that diagnostic application. Moreover, different individual smartphones, types of smartphones, and/or brands of smartphones may have different properties and electronic component responses (e.g., response of the speaker, microphone, and/or processor(s)). Examples described herein may provide systems and techniques which may be utilized to estimate a state of an ear canal notwithstanding variations in the component responses which may be present.

According to various aspects and embodiments of the invention, while examples are described herein with reference to smartphones, it is to be understood that techniques described herein may be implemented on any computing device in some examples. In accordance with some aspects and embodiments of the invention, the computing device used does not require additional components which were specifically designed and designated for acoustic testing of ears. For example, techniques described herein may be utilized to convert a computing device whose primary purpose was not designed to be otologic diagnosis into a device capable of otologic diagnosis. Accordingly, the techniques described herein may be used to adapt the speaker(s), microphone(s), and other components of an existing computing device to be used for analysis of the state of an ear canal. Example computing devices include computers, servers, medical devices. Example computing devices include wearable devices, such as watches, rings, necklaces, pendants, bracelets, hearing aids, smart ear buds, eyeglasses or eyeglass-mounted devices, helmets, and headsets. Computing devices described herein may be Internet-connected devices and/or Bluetooth connected devices with a capability to communicate with other computing devices.

According to various aspects and embodiments of the invention, examples of smartphones described herein, such as smartphone 118, may include one or more speakers, such as speaker 112. The speaker 112 may be in communication with (e.g., electrically connected to) the processor 102. For example, the speaker 112 may be integrated with a device also including the processor 102. In some examples, the speaker 112 may be in wireless communication with a device including the processor 102. The speaker 112 may be used to generate one or more acoustic signals. The speaker 112 may in some examples be integrated with the smartphone 118. In some examples, the speaker 112 may be in electronic communication with the smartphone 118 (e.g., may be connected to the smartphone 118). Examples include when the speaker 112 is provided in an ear bud.

According to various aspects and embodiments of the invention, examples of smartphones described herein, such as smartphone 118, may include one or more microphones, such as microphone 114. The microphone 114 may be in communication with (e.g., electrically connected to) the processor 102. For example, the microphone 114 may be integrated with a device also including the processor 102. In some examples, the microphone 114 may be in wireless communication with a device including the processor 102.

According to various aspects and embodiments of the invention, the microphone 114 may be used to receive one or more reflected waveforms—such as a reflected acoustic waveform and/or reflected calibration waveform in accordance with techniques described herein. The microphone 114 may in some examples be integrated with the smartphone 118. In some examples, the microphone 114 may be in electronic communication with the smartphone 118. While the speaker 112 and microphone 114 are shown incorporated in a same device, in some examples, the speaker 112 and microphone 114 may be located in separate devices.

According to various aspects and embodiments of the invention, in many smartphones, the speaker 112 and microphone 114 may be co-located (e.g., on a same side and/or phase of the smartphone 118). Typically, co-location of the speaker 112 and microphone 114 may be provided to facilitate another function of the smartphone 118, such as voice communication. However, in examples described herein, co-location of the speaker 112 and microphone 114 may be advantageously used to facilitate estimation of state(s) of an ear canal.

According to various aspects and embodiments of the invention, smartphones described herein, such as smartphone 118, may include one or more processors, such as processor 102. Any kind or number of processors may be present, including one or more central processing unit(s) (CPUs), graphics processing unit(s) (GPUs), having any number of cores, controllers, microcontrollers, and/or custom circuitry such as one or more application specific integrated circuits (ASICs) and/or field programmable gate arrays (FPGAs).

According to various aspects and embodiments of the invention, smartphones described herein, such as smartphone 118, may include memory, such as memory 104. Any type or kind of memory may be present (e.g., read only memory (ROM), random access memory (RAM), solid state drive (SSD), secure digital card (SD card)). While a single box is depicted as memory 104, any number of memory devices may be present. The memory 104 may be in communication (e.g., electrically connected) to processor 102.

According to various aspects and embodiments of the invention, the memory 104 may store executable instructions for execution by the processor 102, such as executable instructions for estimate state(s) of ear canal 106. In this manner, techniques for estimating state(s) of an ear canal may be implemented herein wholly or partially in software.

According to various aspects and embodiments of the invention, the memory 104 may store data which may be used by and/or produced by techniques described herein. For example, the memory 104 may store model 108 and/or threshold(s) 110.

While memory 104 is shown as containing executable instructions for estimate state(s) of ear canal 106, memory 104 and threshold(s) 110, those components may be contained on the same memory and/or may be stored on different memories in some examples. According to various aspects and embodiments of the invention, examples described herein may accordingly provide software for estimating a state of an ear canal. Any number of states of an ear canal may be detected and/or analyzed in accordance with techniques described herein including, but not limited to, presence and/or amount of ear wax in the ear canal, presence and/or amount of fluid in the ear canal (e.g., behind an ear drum), presence and/or number of organisms in the ear canal (e.g., bacteria and/or viruses behind the ear drum). Examples of states of an ear canal include mobility of an eardrum in the ear canal. Additional examples of states of the ear canal include disease states—e.g., the presence of acute otitis media (AOM) and otitis media with effusion (OME). Although referred to for simplicity as a state of the ear canal techniques described herein may measure the acoustic impedance of the ear canal, ear drum, middle ear, and inner ear, which can be used for any number of external ear, middle ear, and inner ear diagnoses. Diagnoses include cerumen impaction, OME, AOM, ossicular chain issues, tympanosclerosis, etc. Moreover, techniques described herein may distinguish between these conditions (e.g., by training machine learning models to distinguish between selected conditions). Examples described herein may also be used for acoustic reflex testing, evoked ear potentials, and acoustic emittance.

According to various aspects and embodiments of the invention, while the presence and/or amount of ear wax in the ear canal may be a state that may be determined (e.g., estimated) in accordance with techniques described herein, in some examples the presence of ear wax in the ear canal may not impede techniques described herein in estimating another state of the ear canal. This may advantageously allow methods described herein to be performed in ear canals whether or not they include ear wax (e.g., cerumen) or indeed are wholly or partially occluded by ear wax.

According to various aspects and embodiments of the invention, software for estimating a state of an ear canal may include executable instructions for estimate state(s) of ear canal 106. The executable instructions for estimate state(s) of ear canal 106 may include instructions which may cause the smartphone to perform techniques for estimating the state of the ear canal described herein.

According to various aspects and embodiments of the invention, techniques for estimating the state of the ear canal may include interrogating the ear canal with an acoustic waveform (e.g., which may be provided by speaker 112). In some examples, the speaker 112 may be positioned so it is directed toward the ear canal (e.g., by positioning the smartphone 118 to direct the speaker 112 toward an ear canal). The acoustic waveform may be an audible waveform. The acoustic waveform may include frequency-modulated continuous-wave (FMCW) signals. The FMCW signals may cover a range of frequencies, such as 1.8-4.4 kHz in some examples, 2-4 kHz in some examples, 1.5-3 kHz in some examples, or in other examples signal ranges may be used.

According to various aspects and embodiments of the invention, techniques for estimating the state of the ear canal may include receiving a reflected acoustic waveform (e.g., at microphone 114). The reflected acoustic waveform may be generated by all, or a portion of the acoustic waveform provided by speaker 112 being reflected and/or scattered off an ear drum in the ear canal. For example, during all or a portion of time that the speaker is providing the acoustic waveform 112, the microphone 114 may remain active and may receive both incident signals from the speaker 112 and reflected signals from the eardrum. Sound (e.g., acoustic waveform(s)) reflected from the eardrum will destructively interfere with the incident acoustic waveform (e.g., signal) and cause a dip in sound pressure along a range of frequencies.

A normal eardrum resonates well at multiple sound frequencies, creating a broad-spectrum, soft echo; as a result, the shape of the resulting acoustic dip is broad and shallow in the frequency domain. In contrast, a fluid or pus-filled middle ear, as found in OME and AOM, restricts the vibrational capacity of the eardrum; sound energy that would have vibrated the eardrum is instead reflected back along the ear canal, creating more destructive interference, and resulting in a differently shaped change in the signal (e.g., a narrower and deeper acoustic dip). The change (e.g., the acoustic dip) occurs at the resonant frequency of the ear canal where the quarter-wavelength of the signal is equal to the length of the canal. Thus, while individual differences in ear canal length may affect the location of the dip along the frequency domain, the shape of the dip primarily depends on the state of the ear canal (e.g., the presence or absence of middle ear fluid).

According to various aspects and embodiments of the invention, techniques for estimating the state of the ear canal may include creating a calibrated waveform based on the reflected acoustic waveform. For example, the processor 102 operating in accordance with executable instructions for estimate state(s) of ear canal 106 may adjust a received reflected acoustic waveform in accordance with a calibration signal to provide the calibrated waveform. This calibration procedure may be used to compensate for an open-air behavior of the smartphone 18.

According to various aspects and embodiments of the invention, techniques for estimating the state of the ear canal may include classifying the calibrated waveform as a state of the ear canal. For example, the executable instructions for estimate state(s) of ear canal 106 and/or processor 102 may implement a machine learning technique (e.g., regression) which may classify the calibrated waveform as a particular state. The machine learning technique may utilize one or more models (e.g., model 108) to perform the classification. The model 108 may be generated, for example, by training using the smartphone 118 or another device. Training may be implemented, for example, using waveforms generated in ear canals known to have a particular state.

According to various aspects and embodiments of the invention, in some examples, models may be trained for use with machine learning techniques described herein. A testing device used to implement the machine learning model and classify a waveform from a patient may be different than one or more of the device(s) used to train the machine learning model. For example, training may be conducted using one configuration of device (e.g., an iPhone) while testing may take place using another configuration of device (e.g., a Samsung Galaxy phone) executing a machine learning technique based on the model trained up using the training device(s). Moreover, testing may be conducted using one configuration of soundwave guide while testing may take place using another configuration of soundwave guide. One or more thresholds may be used to interpret and/or adjust an output of a machine learning model for a computing device and/or soundwave guide which was not used to conduct the training.

According to various aspects and embodiments of the invention the classification may be based on a shape of all or a portion of the calibrated waveform. In some examples, a feature may be identified in the calibrated waveform (e.g., a dip). Data regarding the waveform at multiple frequencies of the feature may be used for classification. In this manner, an overall shape of the feature (e.g., the dip) may be used for classification, rather than a single metric such as a height and/or angle of the feature. In some examples, sound intensities (e.g., in decibels) for each frequency along an acoustic feature (e.g., an acoustic dip) may be used as separate features as input to a machine learning technique (e.g., logistic regression). Classification may be performed to associate a calibrated waveform with one or more states of an ear canal (e.g., to estimate the state of the ear canal). The classification may compare the calibrated waveform with known information about various ear canal states (e.g., models generated from training data). For example, weights or other parameters for a machine learning classification may be available to classify a calibrated waveform into any of a variety of ear canal states. For example, acute otitis media (AOM) (e.g., presence of infected fluid with pus) may be detected based on a presence of a deeper dip in ear canals having AOM than having otitis media with effusion (e.g., uninfected fluid). Accordingly, classification based on a depth of an acoustic dip or other feature may be able to discriminate as between infected and uninfected fluid behind an eardrum.

According to various aspects and embodiments of the invention, in some examples, a different smartphone or device type may be used for testing with a model trained based on a different smartphone and/or device type. A testing approach may be used to support the different testing device, which may avoid and/or reduce a need to collect training data (e.g., clinical data) for every new smartphone or device that may utilize techniques described herein. For example, training data may be used to train a model for a trained smartphone or other computing device. This trained model may be nonetheless used to support future devices of the same or different type. Additionally, or instead, training data may be used to train a model for a trained smartphone using a trained soundwave guide. This trained model may be nonetheless used to support future devices using the same or different soundwave guides. One or more thresholds may be identified and used to adjust and/or map a probability or other output of the machine learning technique to an estimate of an ear canal state based on the computing device and/or soundwave guide used to obtain the measurement.

According to various aspects and embodiments of the invention, in some examples, when a new testing device is desired (e.g., different in kind or type or otherwise from the device used to perform the training), the classification technique using the trained model may be tested using the testing device on a number of known targets (e.g., negative ears and/or positive controls). The test may be performed a set number of times each with a set number of soundwave guide instances, assembled from the same template design in some examples. The waveforms may be passed through the trained model. A set of unscaled probability values may be obtained for every test performed in a negative ear and positive control.

According to various aspects and embodiments of the invention, a check may be performed to ensure the probabilities produced for the negative ear do not overlap with the probabilities produced for the positive control. A set of threshold values may then be provided for a given testing device from these unscaled probabilities. There are several ways to select a threshold value. One such method would be the largest probability value produced by the negative ears. Another method would be the lowest probability value produced by the positive control. Yet another method would be the median value between the largest probability value produced by the negative ears and the lowest probability value produced by the positive control. The exact method of threshold determination can vary.

According to various aspects and embodiments of the invention, unscaled probability values below this threshold corresponds to a negative prediction, while being equal to or above this threshold corresponds to a positive prediction. During internal testing, this threshold determination method may be used to produce a threshold for a particular device, e.g., the Samsung Galaxy S6, based on cross-validated data using another device, e.g., the iPhone 5s. With this method, in an implemented example, the clinical accuracies on the Samsung Galaxy S6 on 98 ears were comparable to that produced on the iPhone 5s.

According to various aspects and embodiments of the invention, in some examples, accordingly, the classification may be further based on one or more thresholds. The thresholds may be associated with a particular brand, type, and/or model of smartphone used and/or components of the smartphone used. For example, particular smartphones may vary in their response to an ear canal of a given state. Thresholds may be used to compensate for differences between smartphones and/or smartphone components. For example, a machine learning technique described herein may generate a percentage numerical estimate that an ear canal may have a particular state based on a model or other machine learning information. A threshold may be used to determine what percentage is sufficient for the particular smartphone to identify the ear canal as having the particular state. In accordance with some aspects and embodiments of the invention, smartphones may be tested to determine an appropriate threshold for the smartphone. Thresholds can be set before each measurement session via an in-field calibration process. This may be necessary because a phone's unique wear and tear patterns will uniquely affect the performance of the onboard sensors (e.g., speaker and microphone). Thus, a DSP Equalizer may be used to achieve this calibration, According to various aspects and embodiments of the invention, with unscaled probabilities, an example numerical threshold could be 0.01. However, this does not mean that the likelihood that someone has middle ear fluid is necessarily 1%. The probabilities may be scaled to an index that may more accurately capture the notion of probability of middle ear fluid.

According to various aspects and embodiments of the invention, in some examples, the classification technique initially produces an unscaled probability value between 0 and 1. A value below or above the smartphone-specific threshold is a negative or positive result for fluid, respectively. This unscaled value may then be transformed to an index that is reflective of the likelihood of a state of the ear canal (e.g., middle ear fluid status). To do this, the smartphone-specific threshold is "mapped" to the threshold determined when cross-validating the technique across known ears. That is, the threshold determined when initially training a model.

According to various aspects and embodiments of the invention, for example, suppose the cross-validation threshold was 0.25 and the new smartphone-specific threshold was 0.05. Unscaled values in the range [0.00, 0.05] may be scaled to [0.00, 0.25] and unscaled values in the range [0.06, 1.00] may be scaled to [0.26, 1.00]. This scaled value may be referred to as the "Middle Ear Fluid Index."

According to various aspects and embodiments of the invention, smartphones described herein may include any number of other components, such as other component(s) 116 shown in FIG. 1. Examples of other components include one or more displays, user interfaces, networking interfaces, communication interfaces, etc. A display of the smartphone may, for example, be used to display instructions for performing techniques described herein (e.g., play an instructional video and/or instructional graphics regarding how to assemble a soundwave guide and/or obtain calibration and/or testing signals described herein) and/or an estimate of an ear canal state determined using techniques described herein. A communication and/or networking interface of the smartphone may be used, for example, to transmit data pertaining to models, thresholds, estimated states, and/or other data described herein. The data may be transmitted to one or more other computing devices, for example. In some examples, smartphones described herein may include one or more positional sensors—including, but not limited to, accelerometer(s), gyroscope(s), geomagnetic sensor(s), inertial sensor(s), and/or GPS device(s).

According to various aspects and embodiments of the invention, examples of systems described herein may include a soundwave guide, such as soundwave guide 120. Soundwave guides may also be referred to as waveguides. The soundwave guide 120 may be positioned to direct an acoustic waveform provided by the speaker 112 from the speaker 112 into an ear canal. The soundwave guide 120 may further be positioned to direct a reflected acoustic waveform from the ear canal to the microphone 114. The soundwave guide 120 may be coupled to the smartphone 118 (e.g., taped, adhered, clipped, connected). In some examples, the soundwave guide 120 may be integrated into a case for the smartphone 118. The soundwave guide 120 may be sized to enclose the speaker 112 and the microphone 114.

According to various aspects and embodiments of the invention, the soundwave guide 120 may be cone-shaped, and may be a flattened cone shape in some examples which may conform to an edge of smartphone 118. In accordance with some aspects and embodiments of the invention, the soundwave guide 120 may be flattened for shipping and pop open for attachment to a smartphone 118. In accordance with some aspects and embodiments of the invention, a waveguide design ships fully flat and is then is adhered and formed into a cylindrical shape by the user just before use, rather than "popped" open design.

In accordance with various aspects and embodiments of the invention, the shapes may also be used including cylinders (e.g., pipes), polygonal bases or tips (e.g., squares, rectangles, parallelograms, rhombuses, triangles, pentagons, hexagons etc.), or any other geometric shape (e.g., stars, crosses, crescents, clovers etc.).

According to various aspects and embodiments of the invention, in some examples, one or more acoustic coupling devices (e.g., tubes) may be used to acoustically couple a speaker and/or microphone. For example, a tube may be provided between a speaker and a microphone (of a same or different device). The tube may be used as a soundwave guide described herein and/or may be acoustically coupled to a soundwave guide described herein. In some examples, one or more tubes may be used to couple sound from a speaker to an ear canal and direct sound from the ear canal to a microphone.

According to various aspects and embodiments of the invention a soundwave guide described herein may have a base, a tip, a length, and optional notches. The width of the base can vary and may be sized to surround a speaker, a microphone, or both. In some examples, a width of the base may also span an entire base or surface of a smartphone or other computing device and may exceed the distance between the speaker and microphone. In accordance with some aspects and embodiments of the invention, the tip of the soundwave guide may be sized to be inserted into the opening of an ear canal and/or over an ear. Any sized tip may be used. In some examples, a length of the waveguide may vary, and any length may be used. Notices may optionally be provided to guide the user to fit the waveguide snugly onto the smartphone or other computing device used. An attachment indicator guide may be present on the base of the waveguide (opposite the tip of the waveguide) that may match a similar indicator on the lower portion of the smartphone's 118 display. Another embodiment of the invention for attaching the soundwave guide to the phone shows an outline of the soundwave guide on the phone's screen. The user simply matches a paper soundwave guide to the outline of the guide on the phone's screen.

In accordance with some aspects and embodiments of the invention, the sound waveguide is implemented using paper or paper type product, which is typically not used as medical device or part of a medical diagnostic device. The novelty of using paper in medical applications allows for various advantages, including: ease of manufacturing, flexibility to fit around any phone size, ease of disposability, and ease of distribution via standard mailed envelops. According to various aspects and embodiments of the invention, a soundwave guide may be wholly or partially implemented using pipe(s) (or other shapes). For example, rubber tubing (or other materials) may be coupled to a microphone and/or speaker connected to a computing device. In some examples, a rubber tube may be inserted into a piece of rubber, foam, or other material. The material may be placed over the microphone and/or speaker connected to a computing device. The material may be held in place to the device with any of a variety of materials including, but not limited to, elastic bands, tape, or glue. A more promising material for waveguide construction is paper because it is relatively inexpensive and easy to attach to a smartphone.

According to various aspects and embodiments of the invention, an end of the cone may have a diameter sized to approximate an anticipated size on an ear canal opening while being sufficiently large to allow acoustic signals to pass into the ear canal (e.g., 5 mm in some examples, 10 mm in some examples, 15 mm in some examples, 13 mm in some examples, 18 mm in some examples, and other dimensions may be used). Another end of the soundwave guide may be sized to enclose a microphone and a speaker of the smartphone. Advantageously, the microphone and speaker of many smartphones may be co-located (e.g., because close placement of these components facilitates noise cancellation during voice communication). The base of the soundwave guide cone may vary in size depending on the proximity of the speaker and microphone. For example, in Samsung Galaxy phones, the speaker and microphone are approximately 5 mm apart, such that a smaller conical base may be used. In contrast, they are further apart in iPhones, such that a slightly larger conical base may be used. In one example, a soundwave guide may have a base diameter of 90 mm for the Samsung Galaxy S6 and S7, 105 mm for the iPhone 5s, and 115 mm for iPhone 6s and Google Pixel. For each template, the soundwave guide was sized with a 15 mm diameter opening which approximates the size of the opening into the ear canal.

According to another embodiment of the invention, a paper soundwave guide is a universal size and can be used across a wide spectrum of cell phones makes and models. In accordance with some aspects and embodiments of the invention, the ear tip is narrower than the narrowest phone model width and wider than the widest speaker-microphone distance.

In accordance with some aspects and embodiments of the invention, the paper soundwave guide includes perforations on the ear tip that people can remove, cut, or tear-off to size the ear tip accordingly for their phone in hand.

In accordance with some aspects and embodiments of the invention, the paper soundwave guide is a DIY version that the user cuts or creates using guiding information displayed on the phone. For example, the user turns the phone into a lightbox using a bright white screen with a black outline. The user places any paper on top of the screen. The users see the black outline to trace and then cut out the shape needed to form the paper soundwave guide. This will allow custom sizes for that phone model and does not limit the user's ability to produce or create the paper soundwave guide, especially when the household does not have a printer.

According to various aspects and embodiments of the invention, the soundwave guide may be made from any of a variety of materials. In some examples, the soundwave guide may be made from paper (e.g., filler paper, inkjet paper, laser-jet paper, cardstock). In some examples, the soundwave guide may be made wholly or partially of silicone, plastic, metal, fabric, rubber, glass, aluminum, wood, or concrete. The soundwave guide may be disposable in some examples. The soundwave guide may not be disposable in some examples.

According to various aspects and embodiments of the invention, the soundwave guide 120 may be made of a foldable material in some examples, such as paper and/or plastic. In some examples speaker 112 and/or microphone 114 may be present in an ear bud connected to the smartphone 118 and the soundwave guide 120 may be arranged to enclose the ear bud, such as by enclosing a speaker 112 at an outer edge of the soundwave guide 120 and the microphone 114 at an inner edge of the soundwave guide 120. In some examples, the smartphone 118 may include a handheld communication device or a mobile device, or some auxiliary speaker and microphone such as in a wired headset or a wireless headset.

According to various aspects and embodiments of the invention, in some examples, the soundwave guide may be low-cost and simple to generate by a potential user of the system. For example, the soundwave guide may be implemented using a conical paper waveguide which may be cut from a printed paper template. The soundwave guide may alternatively be manufactured at a facility, packed, and shipped flat (to reduce costs) to medical clinics and to telemedicine patient's homes. Where the shipped soundwave guides can simply be popped open and attached to speaker 112/microphone 114 end of a smartphone 118 to conduct the diagnostic test for AOM or OME.

Referring now to FIG. 2 along with FIG. 1, according to various aspects and embodiments of the invention, the system of FIG. 1 is shown for determining whether there is fluid 214 in a child's middle ear. The system 200 includes smartphone 202, soundwave guide 204, and ear canal 206. The ear canal 206 may include eardrum 208 and there may be fluid 214 present behind eardrum 208. During operation, the smartphone 202 may deliver acoustic waveform 210 into the ear canal 206 and may receive reflected waveform 212 reflected from the eardrum 208. The state of the ear canal (e.g., the presence and/or absence of fluid 214) may produce characteristic features in signals received at the smartphone 202. The smartphone 118 of FIG. 1 may be used to implement smartphone 202 of FIG. 2. The soundwave guide 120 of FIG. 1 may be used to implement soundwave guide 204 of FIG. 2. The components shown in FIG. 2 are exemplary. Additional, fewer, and/or different components may be used in other examples.

During operation, the soundwave guide 204 may be coupled to the smartphone 202. For example, the soundwave guide 204 may be clipped, adhered, or otherwise attached to smartphone 202 in a manner which encases a microphone and speaker of the smartphone 202.

The tip of the soundwave guide 204 may be positioned at the entrance of (e.g., into) the patient's ear canal 206. In some examples, the soundwave guide 204 may point medially and slightly anteriorly into the ear canal 206. In some cases, the ear canal 206 may be straightened during testing by gently pulling the pinnae posteriorly. In some examples, one or more positional sensor(s) on the smartphone 202 may be used to aid in positioning of the soundwave guide 204 into the ear canal 206. For example, the smartphone 202 may display an indication when the smartphone is oriented off of horizontal. In accordance with some aspects and embodiments of the invention, the phone's gyrometer determines if the smartphone is improperly aligned to the ear canal. This process using a classifier-based diagnostic tool in conjunction with the gyrometer and ensures that the reflected signal looks like what is expect to be received from a signal that is reflected from an ear a canal, e.g., is not a blocked tip by pointing straight into the ear's skin rather than into the ear canal, or by virtue of having a foreign body in the ear blocking the canal.

For example, the smartphone 202 may display a number of degrees titled from horizontal the smartphone may be (e.g., 5°, 10°, etc.). The display may indicate an unacceptable variation from horizontal when the deviation is greater than a threshold (e.g., 45° in some examples, 30° in some examples). The display may indicate that the smartphone may be oriented so as to be inserted into the ear of a supine patient rather than an upright patient. The display, or other output of the smartphone, may prompt a user to change to a measurement of an upright patient, such as by playing recorded speech instructions, or displaying instructions to a user. Accordingly, the smartphone 202 may be positioned such that the speaker is oriented horizontally or within 45° of horizontal in some examples, within 30° in other examples, and other angles may be used.

During operation, the smartphone 202 may direct an acoustic waveform 210, such as one or more frequency signals, from a speaker into the patient's ear canal 206. In some examples, the smartphone 202 may direct the acoustic waveform 210 into the patient's ear canal 206 through the soundwave guide 204. In some examples, the acoustic waveform 210 may include audible, 150 ms modulated continuous-wave (FMCW) signals from 2.0-2.8 kHz. In some examples, the acoustic waveform 210 may be from 2.3-3.8 kHz. In some examples, the acoustic waveform 210 may be from 1.84.4 kHz. In some examples, the acoustic waveform 210 may be played for a duration of 20, 50, 100, 200, 250, 300, 350, or 400 ms. Other durations may also be used. Multiple signals may be played during the duration, including repeating the signals over a same frequency range or other frequency ranges. In accordance with some aspects and embodiments of the invention, complex sounds may be used that involve rudimentary melodies coupled with white noise.

A sequence of 10 signals may be played in some examples, with other numbers of repetition used in other examples. In one example, 10 identical signals may be provided with a frequency range of 1.8 kHz to 4.4 kHz, each for a duration of 150 ms. Each signal may be interspersed with a time of silence, 250 ms of silence in one example, although other amounts may also be used. In some examples, the acoustic waveform 210 may imitate the sound of a bird to create a calming effect for the patient. While noises within signal frequencies may impact accuracy of the results, ambient noises may typically be outside the signal frequencies. For example, an infant crying may reach only 400 Hz. In some examples, crying or other unwanted noises may be wholly and/or partially cancelled using components such as low pass filters, high pass filters, band pass filters as well as adaptive filters such as least mean squares filters. Therefore, the crying noise may not impact the techniques described herein.

In some embodiments, readings from one or more sensors of the smartphone (e.g., accelerometer, gyroscope, the speaker (due to garbled signal), and/or geomagnetic sensors), may indicate significant movement or change in orientation of the smartphone during the course of several signals during the measurement (e.g., due to the patient head or body moving too much or the smartphone moving too much). In some embodiments, the smartphone may be programmed to provide an indication to the user to repeat a measurement if an amount of movement or ambient noise during the measurement was detected above a threshold.

A microphone of the smartphone 202 may receive a reflected waveform 212 responsive to the acoustic waveform 210 reflected from the patient's eardrum 208. For example, the smartphone may, at least partially, simultaneously with the providing of the acoustic waveform, record audio from the microphone for a period of time (e.g., 10s in some examples, although other times may also be used). A sampling rate of 48 kHz was used in one example, although other sampling rates may also be used. In some examples, the microphone may receive the reflected waveform 212 through the soundwave guide 204 (e.g., through the aperture of the apparatus that may be wholly and/or partially disposed in an ear canal. The reflected waveform 212 may destructively interfere with the incident acoustic signal and may cause features (e.g., a dip in sound pressure) along a range of frequencies. The feature (e.g., acoustic dip) may occur at the resonant frequency of the ear canal where the quarter-wavelength of the acoustic signal is equal to the length of the canal. Therefore, while individual differences in the ear canal 206 between patients may affect the location of the dip along the frequency domain, the shape of the dip primarily reflects the state of the ear canal 206.

Various processing may occur on the reflected waveform 212. For example, cross-correlation may be performed between the reflected waveform 212 and the acoustic signal to find a starting sample of each signal in the reflected waveform 212. For each signal, a transform (e.g., a 48,000 point or other resolution Fast Fourier Transform) may be performed to provide a frequency response. In one example, the frequency response may be found from 0-24 kHz, although other frequency ranges may be used. Frequencies outside of the transmitted signal range (e.g., outside of 1.8-4.4 kHz in some examples) may be discarded. Signals that were two or more standard deviations from the mean of all recorded signals may be excluded from further analysis. In some examples, only certain signals may be analyzed, and the remainder excluded.

The reflected waveform 212 (e.g., a combination of the reflected waveform 212 and the incident acoustic waveform 210) may be adjusted based on a calibration to provide a calibrated waveform. The calibration may occur prior to interrogation of a particular ear canal and may be particular to the smartphone 202 used for interrogation. The calibration may be used to reduce variations in the received waveform caused by the particular arrangement of the smartphone used and/or environment. For example, a calibration procedure may be used which generates a response of the smartphone components in a calibration environment (e.g., a finger causing blocking of the tip or in the absence of an ear canal) or with a finger blocking the tip of the soundwave guide. A combination of the reflected waveform 212 and signals generated during the calibration process may therefore provide a calibrated waveform which may be more reliably classified, having smartphone specific and/or environment specific features in the waveform reduced and/or eliminated.

In some embodiments, filtering may be used to smooth the reflected waveform 212 and/or the calibrated waveform. A feature-detection algorithm (e.g., a peak detection algorithm) may be used identify the feature (e.g., acoustic dip) associated with sound waves being reflected off the eardrum. For example, the most prominent features (e.g., acoustic dips) may be identified within a frequency range, such as within 2.3-3.8 kHz in some examples. Frequencies within a range of the frequency of the feature (e.g., within 500 Hz of the feature in some examples) may be utilized for further processing. In this manner, machine learning techniques may be focused on data associated with the portions of the acoustic response most predictive of a state of the ear canal (e.g., middle ear effusion status).

The calibrated waveform according to some embodiments, may be classified based on a machine learning technique to estimate a state of the ear canal 206 using a shape of the calibrated waveform.

An estimated state of the ear canal may be displayed to a user (e.g., on a display of the smartphone 202). For example, a display may indicate that fluid is present in the ear canal. A display may indicate that bacteria is present in the ear canal. A display may indicate that a viral load is present in the ear canal. The estimated state of the ear canal may additionally or instead be stored (e.g., in a memory accessible to the smartphone 202) and/or may be transmitted to another computing device (e.g., to a computing device accessible to a healthcare provider). In some examples, a text-based message may be presented on a display to the user indicating a result: e.g., "suggestive of middle ear fluid" or "middle ear fluid unlikely."

Referring now to FIG. 3, FIG. 2, and FIG. 1, according to various aspects and embodiments of the invention, shows a schematic illustration of a system arranged in accordance with examples described herein. FIG. 3 depicts smartphone 302 during a calibration process. The smartphone 302 may be coupled to soundwave guide 304, which may enclose a microphone and speaker of the smartphone 302. The smartphone 302 may provide calibration signal 306 and receive reflected calibration waveform 308 from a calibration environment. The smartphone 302 may be implemented using the smartphone 118 of FIG. 1 and/or smartphone 202 of FIG. 2. The soundwave guide 304 may be implemented using the soundwave guide 120 of FIG. 1 and/or soundwave guide 204 of FIG. 2. The components of FIG. 3 are exemplary only, and additional, fewer, and/or different components may be used.

An example calibration process is described with reference to FIG. 3. The calibration process may in some examples be performed using a same smartphone as will be used to provide acoustic signals to an ear canal for estimation of the ear canal state. Moreover, in some examples the calibration process may be performed in an environment similar to the environment in which signals will be provided to an ear canal (e.g., in a same room, building, and/or city).

In some examples, the calibration may be performed by a different smartphone than will later use the calibration results to estimate an ear canal state, and data regarding the calibration may be provided to the smartphone used to estimate ear canal state (e.g., by storing calibration data in a location accessible to the smartphone). The calibration may preferably be performed by a smartphone having a same brand, type, or model as the smartphone used to estimate ear canal state. In accordance with some aspects and embodiments of the invention, the age or wear of the smartphone is also taken into consideration when performing calibrations.

Calibration may be performed prior to providing acoustic signals to an ear canal for use in estimating an ear canal state. However, in some examples, waveforms may be received from an ear canal, data may be stored regarding the received waveforms, and calibrated in accordance with later-received calibration information. Accordingly, in some examples, a calibration procedure may be performed after providing acoustic signals to an ear canal.

The calibration procedures may be used to reduce the variability caused by different waveguides as well as microphone and speaker differences across smartphones. Calibration may be desirable and/or necessary to improve an ability of a machine learning technique to later classify a resulting calibrated waveform. For example, without calibration, the received waveforms may vary in accordance with particular smartphones such that it may be difficult or impractical to classify them using a trained machine learning technique.

During calibration, the smartphone 302 (e.g., a speaker of the smartphone 302) may direct a calibration signal (e.g., a signal) into a calibration environment through a soundwave guide 304. The calibration signal may be similar (e.g., the same) as an acoustic signal that will be provided to an ear canal. For example, the calibration signal may be an acoustic signal including one or more frequency signals. the frequency signals may occur at the same and/or overlapping frequencies to those used to interrogate an ear canal for estimating ear canal state.

The calibration environment may be an open-air environment (e.g., an environment providing minimal reflected waves), or a fully blocked environment by using a fingertip or other hard surface to block the signal. In some examples, the calibration environment may be a known environment for which reflection properties are understood, such as a known ear canal, simulated ear canal (e.g., plastic tube), or other material. The smartphone 302 may receive a reflected calibration waveform 308 responsive to the calibration signal through the soundwave guide 304, reflected from the calibration environment. The reflected calibration waveform 308 may be used for calibrating signals received during interrogation of an ear canal. For example, the reflected calibration waveform 308 may be normalized by combining the calibration signal 306 and the reflected calibration waveform 308 to determine a baseline signal. The baseline signal may represent a unit frequency response of the speaker and microphone of the smartphone 302 and the soundwave guide 304.

Referring back to FIG. 2, the reflected waveform 212 obtained during testing may be adjusted based on the reflected calibration waveform 308 and/or the baseline signal to provide the calibrated waveform used for classification. For example, the reflected waveform 212 may be scaled and/or combined with the reflected calibration waveform 308 and/or baseline calibration signal 306. In some examples, a set of weights may be generated based on the baseline signal, and the weights may be used to normalize measurements received from a patient's ear canal.

The weights and/or other information about the baseline may be stored, for example in memory 104 of FIG. 1. Instructions for performing calibration and obtaining the baseline signal and/or weights may be included in executable instructions for estimate state(s) of ear canal 106 of FIG. 1 in some examples.

Referring now to FIG. 4, according to various aspects and embodiments of the invention shows, a graphical illustration of example reflected waveforms obtained when an example acoustic signal is played into a patient's ear canal in accordance with examples described herein for both an ear canal with fluid behind the eardrum and without. The raw waveform of an eardrum full of fluid 404 has a more prominent acoustic dip. A bottom of the dip is indicated along the raw waveform of an eardrum full of fluid 404 using a prominent dot in FIG. 4. The raw waveform of a normal eardrum 402 with a shallower acoustic dip may occur at a higher frequency due to an effectively shorter canal and corresponding quarter-wavelength. A bottom of the dip is indicated along raw waveform of a normal eardrum 402 using a prominent dot in FIG. 4. Typically, a number of points of data making up the dip may be used for classification. The waveforms of FIG. 4 are provided by way of example of the kinds of changes in reflected waveforms which may be caused by different ear canal states. It is these changes that the techniques and systems described herein may utilize to classify waveforms.

Referring now to FIG. 5, FIG. 4, and FIG. 1, according to various aspects and embodiments of the invention shows, a graphical illustration of a calibrated acoustic waveform arranged in accordance with examples described herein. As shown in FIG. 5, the graphical representation of a calibrated acoustic waveform is an adjusted (e.g., smoothened) curve as compared to the raw acoustic waveform shown in FIG. 4. The calibrated acoustic waveform may represent an output of a moving average window. For example, a moving average filter with a window size. In some examples, the window size may be 300 samples. Other window sizes may be used including, but not limited to, 100, 150, 200, 250, 350, 400, 450, 500 samples. The filter may be implemented, for example, by any smartphone described herein.

Once the most prominent feature (e.g., dip) within a particular frequency range in the calibrated acoustic waveform is identified, some number of frequency points on either side may be collected and used for classification. For example, 500 points to the left and 500 points to the right of the dip 502 of FIG. 5 may be collected and analyzed. The number of points measured around the dip is not limited to 500. For example, the number can be 100, 200, 400, 800, 1200, 1600, or another number may be used. These point values may form an array where each element may represent the amplitude for each of the selected frequencies around the acoustic feature (e.g., dip 502). Each of the acoustic signals may be aggregated into a single matrix. Using a logistic regression machine learning algorithm, each of the points collected may be assigned a weight to determine the state of the ear canal. The depth of the acoustic dip may be given the most weight in some examples. Models described herein may specify the weights, such as model 108 of FIG. 1. For example, machine learning techniques described herein may be trained to develop a set of weights—with a weight associated in some examples with each point (e.g., frequency) from a set of points collected which represent an acoustic feature (e.g., acoustic dip). Sound intensities at the top and bottom of the acoustic waveform may be given the most weight by the predictive model. Accordingly, an acoustic pattern may be independently identified for middle ear fluid consistent with the known acoustic response of the eardrum. The model may be trained with data collected from patients or other sources using the respective smartphone and/or a different smartphone.

Referring now to FIGS. 6A-C and FIG. 1, according to various aspects and embodiments of the invention show, graphical illustrations of examples of cerumen occlusions in accordance with examples described herein. Examples described herein may alert users to the presence of cerumen (e.g., ear wax) and/or may accurately estimate a state of an ear canal notwithstanding the presence of cerumen in the canal. The graphs of FIGS. 6A-C illustrate waveforms generated in a model ear utilizing putty to mimic cerumen and demonstrate the type of changes cerumen may make to waveforms described herein. FIG. 6A illustrates a situation where there is partially occluding wax (60-70%) in the model ear. The partial occlusion had little effect on the shape or position of the features indicative of the state of the ear canal. For example, waveform 602 was gathered when there was no occlusion in the model ear. Waveform 604 was gathered when there was a 60% occlusion measured at 0 cm deep in the model ear. Waveform 606 was gathered when there was a 60% occlusion measured at 1 cm deep. A shape and position of a feature (e.g., acoustic dip) may be similar among the three waveforms: waveform 602, waveform 604, and waveform 606. Accordingly, techniques described herein may be insensitive to partial occlusions.

FIG. 6B illustrates a situation where there is 100% cerumen occlusion (e.g., impaction). As the site of impaction moves closer to the entrance of the ear canal, a relevant feature (e.g., acoustic dip) may appear shallower and occur at a higher frequency due to an effectively shorter canal and corresponding quarter-wavelength. Waveform 608 illustrates an ear with no occlusion. Waveform 610 illustrates an ear with 100% occlusion measured at 0.5 cm deep. Waveform 612 illustrates an ear with 100% measured at 1 cm deep. In these cases, signals can reflect off cerumen, generating a false feature (e.g., acoustic dip) that may not be representative of middle ear status. For example, at a depth of 1 cm, which is the deepest point cerumen would naturally accumulate, a false acoustic dip is shown in waveform 612 located approximately 1 kHz higher compared to a normal dip from eardrum reflections in waveform 608. At shallower depths of impaction, the false dip was even more right-shifted, as shown in waveform 610. Accordingly, examples described herein may provide an error or alert if a feature (e.g., acoustic dip) is identified at a frequency that is outside of an expected range. For example, an acoustic dip representative of middle ear status may be expected at around 3 kHz in some examples (e.g., between 2.4-3.7 kHz). An alert may be displayed and/or provided when a feature (e.g., acoustic dip) is instead identified outside this range. Moreover, a shallow cerumen occlusion may generate a reflected waveform similar to that reflected responsive to a calibration signal (e.g., similar to an open-air calibration environment).

FIG. 6C illustrates this scenario, with waveform 614 corresponding to data generated responsive to a calibration signal in an open-air calibration environment. The waveform 616 corresponds to data reflected from an ear with 100% occlusion at 0 cm deep. Accordingly, in some examples, systems described herein may provide an alert when a reflected waveform 620 resembles a reflected calibration waveform 622.

The system of FIG. 1 may be arranged to provide the cerumen-related alerts described herein. For example, the executable instructions for estimate state(s) of ear canal 106 may include instructions for determining whether a feature is outside of an expected range and/or if a reflected waveform resembles a reflected calibration waveform and providing the corresponding alert. The alert may be displayed on the smartphone, may be implemented using an audible tone and/or spoken alert, and/or may be stored and/or transmitted to another computing device. Diagnosis and treatment of middle ear infection currently has necessitated astute clinical decision-making. For example, prescribing antibiotics for acute otitis media may utilize clinical context apart from the presence of middle ear fluid, such as infection severity, time-course, and systemic symptoms. For recurrent infections and persistent effusions, referral to a specialist is recommended for possible surgical management. However, even after initial physician consultation, patients may require repeat visits to monitor middle ear fluid, which can result in high utilization of healthcare systems. Under physician guidance, technology described herein may allow laypersons (e.g., parents or patients) to monitor an ear canal for fluid behind the ear drum or excess ear wax in the ear without purchasing additional medical hardware.

Implemented Example: An implemented example system was used in a 98-patient-ear study including pediatric patients between 18 months and 17 years of age were drawn from two different subgroups: i) patients undergoing ear tube placement, a common surgery performed on patients with chronic OME or recurrent AOM (n=48 ears), and ii) patients undergoing a different surgery, such as tonsillectomy, without recent symptoms of AOM or OME and without signs of middle ear fluid on physical examination (n=50 ears). A receiver-operating characteristic (ROC) curve was generated from the cross-validation step, with an area under the curve (AUC) of 0.865. The operating point was chosen to have an overall sensitivity and specificity of 84.6% (95% CI: 65.1-95.6%) and 80.6% (95% CI: 69.5-88.9%), respectively. With K-fold (K=10) cross-validation, a comparable AUC of 0.847 was obtained.

The algorithm predicted that ears with narrower and deeper acoustic dips were more likely to have middle ear fluid. Similarly, on univariate analysis, sound intensities at the top and bottom of the waveform, which determine the depth of an acoustic dip, were given the most weight by the predictive model). Acoustic reflectometry, which also assesses middle ear fluid status, demonstrated an AUC of 0.774, similar to previously published results. Therefore, the smartphone algorithm's improved clinical performance may be the result of applying machine learning over the waveform rather than relying on a few hand-selected features used by acoustic reflectometers.

Data for the study was collected using both the iPhone 5s and the Samsung Galaxy S6. Specifically, the entire iPhone 5s dataset was used for training except for one patient ear which was "held out" for testing. The trained algorithm was then tested on Galaxy S6 data from the held-out ear. This was repeated for all patient ears in the cohort to generate an AUC of 0.858. In the same manner, testing was also performed on a subset of the patient cohort using an iPhone 6s (n=10 ears), Samsung Galaxy S7 (n=12), and Google Pixel (n=8). The algorithm correctly classified 80% (8 of 10) of iPhone 6s, 91.7% (11 of 12) of Galaxy S7, and 87.5% (7 of 8) of Pixel data.

The usability of the soundwave guide was tested on 10 untrained adults. The 10 participants were shown a short instructional video and were asked to create and mount a soundwave guide using a paper template, tape, and scissors. The average time required to cut, fold, and attach the smartphone-mounted waveguide was 2.8 (±0.89) minutes. Second, participants tested their waveguide on the ear of a subject who had no middle ear effusion. The same subject's ear was used for testing by all participants to ensure consistency of results. Raw acoustic waveforms generated from a single subject's ear were similar for both untrained and trained users. Furthermore, the algorithm correctly classified all curves as not having middle ear effusion. For the overall system, participants gave an average usability rating of 8.9 (±1.0) on a scale of 1 (unusable)-10 (extremely usable).

Referring now to FIG. 7, FIG. 1, FIG. 2, and FIG. 3, according to various aspects and embodiments of the invention shows, a schematic illustration of an example earbud in accordance with examples described herein. The example of FIG. 7 illustrates a microphone 704 and speaker 706 of an earbud. The earbud may be used to implement the speaker 112 and/or microphone 114 of FIG. 1 in some examples. The earbud of FIG. 7 may be used to implement the speaker and microphone of the smartphone 202 of FIG. 2 in some examples. The earbud of FIG. 7 may be used to implement the speaker and microphone of the smartphone 302 of FIG. 3 in some examples.

Referring now to FIGS. 8A and 8B, according to various aspects and embodiments of the invention shows, schematic illustrations of a smartphone coupled to a soundwave guide 804 having an opening 812 in accordance with examples described herein. FIG. 8A illustrates smartphone 802 have a lower edge 810. A microphone 806 and speaker 808 may be co-located at the edge 810 as shown in the side view having a straight-on view of edge 810. In FIG. 8B, soundwave guide 804 is attached to smartphone 802. The front view shows the conical soundwave guide 804 coupled to the smartphone 802. The side view having a straight-on view of edge 810 depicts the flattened nature of the soundwave guide 804, such that the soundwave guide 804 may be conformed to a shape of the edge 810 and encompass the microphone 806 and speaker 808. An opening is provided in the conical shape of soundwave guide 804 that may be sized to be placed just outside the ear canal.

The smartphone 802 of FIG. 8A and FIG. 8B may be implemented using any smartphone described herein, including smartphone 118 of FIG. 1, smartphone 202 of FIG. 2, and/or smartphone 302 of FIG. 3. The soundwave guide 804 may be implemented using the soundwave guide 120 of FIG. 1 and/or soundwave guide 204 of FIG. 2 or soundwave guide 304 of FIG. 3. The components of FIG. 8A and FIG. 8B are exemplary. Additional, fewer, and/or different components may be used in other examples.

Referring now to FIG. 9, according to various aspects and embodiments of the invention shows, a schematic illustration of a case with and without a smartphone arranged in accordance with examples described herein. The case 902 may be made of any of a variety of materials, such as silicone, and may be sized to enclose a smartphone. The 902 may be integrated with a soundwave guide 904. The soundwave guide 904 may be made of a same or different material than the remainder of the case 902 and may be made of any material, including those described herein. The soundwave guide 904 may be positioned to enclose a speaker and/or a microphone of the device to be placed in the case 902. FIG. 9 contains a second view showing a smartphone 906 placed in the case 902. The soundwave guide 904 may be detachable or not detachable from the case 902.

Referring now to FIG. 10, according to various aspects and embodiments of the invention shows, a schematic illustration of a template for a soundwave guide arranged in accordance with examples described herein. The template 1002 includes an outline for cutting out the apparatus. The template 1002 has a hemispherical shape which may be folded into a cone, so as to form, for example, soundwave guide 404 of FIG. 4. The template 1002 includes notch 1004, notch 1006, canal opening 1008, and overlap indicator 1010. The template may be printed and/or provided on any of a variety of materials including paper, plastic, and/or metal.

The notch 1004 and notch 1006 may be provided and sized to accommodate portions (e.g., corners) of a smartphone or other device housing adjacent a microphone and/or speaker to be enclosed by the acoustic focusing device.

The canal opening 1008 may be sized for placement at the opening of an ear canal, such as using a diameter of between 5 and 10 mm in some examples. The overlap indicator 1010 may provide an indicator (e.g., a dashed line, arrows, or other indicator) of where to adhere an edge of the template to assemble a flattened cone apparatus 1012.

To assemble a soundwave guide, a flat template may be cut, as shown in the first illustration of FIG. 10. The template would be cut along the solid lines, for example. The cut-out template is shown in the next illustration of FIG. 10. The cut template may then be rounded and/or folded into a conical shape as shown in the next illustration of FIG. 10. The ends of the cut template may be positioned to overlap in a region bordered by the overlap indicator 1010. The ends of the cut template may then be adhered to one another, as shown in the next illustration of FIG. 10. The ends may be adhered by any of a variety of mechanisms—including tape, adhesive, glue, staples, clips, slotted assembly, etc. Any of a variety of manufacturing methods may be used to create the soundwave guide including any type of printing, cutting, and adhering. In some examples, soundwave guides described herein may be injection molded and/or 3D printed.

Referring now to FIG. 11A, 11B and FIG. 14, according to various aspects and embodiments of the invention shows, in FIG. 11A, a manufactured paper pop-open soundwave guide 1102A. The paper pop-open soundwave guide is inexpensive to produce and inexpensive and easy to ship because it is produced in a flattened state. FIG. 11B shows the same manufactured paper pop-open soundwave guide in its popped open state 1102B for attachment to a smartphone for diagnostic testing of the ear canal.

To open the flattened paper pop-open soundwave guide 1102A a user simply squeezes a corner 1104 toward a corner 1106. The flattened soundwave guide 1102A pops open into a ready to use soundwave guide 1102B. The popped open soundwave guide 1102B is then attached to a smartphone.

Referring now to FIG. 12 and FIG. 11B, according to various aspects and embodiments of the invention shows, a user attaching the pop-open soundwave guide 1206 to a smartphone 1202. After attaching the pop-open soundwave guide 1206 to a smartphone 1202, it can be secured by an adhesive strip 1204. The details of the adhesive strip 1204 are shown in excerpt AA. Excerpt AA shows three components of the adhesive strip 1204. The components include, an adhesive surface 1204C, a protective cover 1204A, and a pull tab 1204B. The protective cover 1204A prevents the adhesive surface 1204C from sticking to other pop-up soundwave guides 1206 during shipping and to other surfaces during handling. The pull tab 1204B allows a user to easily remove the protective cover 1204A from the adhesive surface 1204C while securing the pop-up soundwave guide 1204 to the smartphone 1202. In other embodiments, a small piece of tape or a rubber band can be used to attach the pop-open soundwave guide 1206 to the smartphone 1202.

Attaching the pop-open soundwave guide 1206 to the smartphone 1202 is straightforward. The user simply pops open the soundwave guide as shown in FIG. 11B by: (1) squeezing corner 1104 toward corner 1106: (2) removing the non-adhesive cover strip cover 1204A; by pulling the adhesive strip tabs 1204B on both the front and back if the soundwave guide that cover the adhesive strips 1204C, placing the pop-up soundwave guide 1206 in proper position on the smartphone 1202; and pressing the adhesive strip surfaces 1204C against the back and front of the smartphone 1202.

Referring now to FIG. 13, FIG. 12, and FIG. 14, according to various aspects and embodiments of the invention shows, the speaker 1304A, 1304B and microphone 1306A, 1306B locations on two models (iPhone XR 1302A and iPhone 8 1302B) of one brand of smartphone, and the speaker 1304C and microphone 1306C locations on a different brand of smartphone (Samsung S9 1302C). The proximity of the speaker to the microphone and their respective locations on the base of a smartphone informs the user how to install the pop-open soundwave guide 1206 as shown in FIG. 14 and FIG. 12.

Referring now to FIG. 14, FIG. 13, and FIG. 12 according to various aspects and embodiments of the invention shows, the correct placement of the pop-open soundwave guide 1206 onto the iPhone XR 1302A and iPhone 8 1302B, and the correct placement of the pop-open soundwave guide 1206 onto the Samsung S9 1302C.

The speakers 1304A, B on the iPhone XR 1304A and on the iPhone 8 1304B are near the bottom left corner of the iPhone models as viewed when facing the smartphone screen while holding the smartphones in a vertical position (with bottom down), and the microphones 1306A, B are near the bottom right corner of the iPhone models 1304A, B.

For optimal diagnostic testing for AOM and OME the pop-open soundwave guide 1206 is attached straight onto the base of the iPhones 1302A, B with the narrow end of the soundwave guide cone 1402 pointing directly downward on a vertically positioned iPhone 1302A, B. On the other hand, the speaker 1304C is located on the right side (when facing the smartphone screen) of the bottom of the Samsung S9 just medially from the smartphone's microphone 1306C which is located on the base of the Samsung S9 adjacent to its right-hand corner. For optimum testing for AOM and OME using the Samsung S9 the pop-open soundwave guide 1206 is properly attached over the bottom right corner (when facing the smartphone screen) of an upright positioned Samsung S9, 1302C where both the speaker 1304C and the microphone 1306C are located. When the pop-open soundwave guide 1206 is properly attached to the Samsung S9 1302C, the soundwave guides small opening 1402 will be pointing diagonally down and to the right of the screen of the vertical face of the Samsung S9 1302C.

Referring now to FIG. 15, according to various aspects and embodiments of the invention shows, the alignment mark 1506 on the smartphone screen 1502A and 1502B and the counterpart alignment mark 1508 on the pop-open soundwave guide 1504.

For a user to properly attach the pop-up soundwave guide 1504 to a smartphone he/she needs to match the alignment mark 1506 on the soundwave guide 1504 to the alignment mark 1508 on the smartphone screen 1502 A and the smartphone screen 1502B. Once the marks are aligned, the user adheres the soundwave guide onto the base of the smartphone.

Another embodiment of the invention uses an outline of the top section of the soundwave guide that a user aligns a paper soundwave guide with to ensure a proper fit over the base of the smartphone.

Referring now to FIG. 16 and FIG. 1, according to various aspects and embodiments of the invention, shows a schematic illustration of an example method arranged in accordance with examples described herein. In some examples, various actions may be performed during an initialization phase to prepare for testing a patient. For example, in the initialization phase 1602 of FIG. 16, a smartphone model may be identified (e.g., a brand, model of device and/or a brand and/or model of speaker and/or microphone). A template for a soundwave guide (e.g., a funnel) may be printed and/or obtained. The soundwave guide (e.g., waveguide) may be assembled. In some examples, the soundwave guide may be assembled using instructions, which may be displayed in some examples by a smartphone application to be used for testing. The soundwave guide may be a pop-open soundwave guide sent to the patient's caregiver by a telemedicine clinic. The pop-open soundwave guide may be sent to the provider by the manufacturer. The instructions for attaching the soundwave guide may be shown by a smartphone application video. The soundwave guide may be attached to the smartphone.

In some examples, various actions may be initiated by the smartphone application during a testing phase for testing a particular patient. For example, in testing phase 1604, a calibration signal may be played into a calibration environment (e.g., open air). An entrance to the ear canal may be located, recording may be initiated on the smartphone by the smartphone application, and the soundwave guide tip may be directed medially and anteriorly into the ear canal. In some examples, the pinnae may be pulled posteriorly to facilitate acoustic access to the ear canal. Acoustic signals (e.g., signals) may be delivered to the ear canal. During delivery of the acoustic signals, received signals may be recorded by a microphone of the device used for testing. When the acoustic signals are finished playing—which may be indicated, for example, by an indicator on a display of the smartphone application and/or sound played by the smartphone—the soundwave guide (which may be connected to the smartphone) may be removed from the ear canal.

In some examples, various actions may be directed by the smartphone application and performed during a processing phase to process signals received during testing. For example, in processing phase 1606, signals in the received acoustic signals may be identified in the time domain and transformed (e.g., using a fast Fourier transform) to the frequency domain. Outlier and/or noisy signals may be discarded, and the signals may be normalized using the signals received during calibration (e.g., responsive to the calibration signal in the calibration environment). An acoustic feature (e.g., acoustic dip) may be identified, and may be classified (e.g., using logistic or other regression). The classification may in some examples provide a probability of a particular diagnosis (e.g., middle ear fluid). In some examples, a threshold may be used which may be specific to the smartphone model or type which may relate the classification probability to an ultimate estimate of the ear canal state. An output of the estimated ear canal state may be provided—such as output 1608 "middle ear fluid unlikely" or output 1610 "suggestive of middle ear fluid" by the smartphone application on the smartphone screen.

The example of FIG. 16 is exemplary only. Other phases may be used in other examples and fewer, additional, and/or different actions may be performed during each depicted phase. The executable instructions for estimate state(s) of ear canal 106 of FIG. 1 may include instructions for performing the delivery of calibration and/or other acoustic signals during the testing phase 1604 and the actions depicted as occurring during the processing phase 1606.

Referring now to FIG. 17A, B, FIG. 16, FIG. 15, FIG. 13, FIG. 2, and FIG. 1, according to various aspects and embodiments of the invention, shows examples of the various smartphone application instructional displays that may appear on the smartphone screen. During the initiation phase 1604, the smartphone application is installed and opened on a smartphone and a "Log On or Sign Up" screen 1702 is displayed. After a user signs up for the application 1702, a license agreement page appears where the user either agrees or disagrees with the terms and conditions of use.

In one embodiment of the invention, once a user signs up or logs onto the smartphone application, the smartphone application may identify the type of smartphone being used and displays its make and model on the smartphone screen 1704.

Here, the smartphone application may ask, "Who needs a scan?" and may include spaces for photographs of the user's children. The user simply touches one of the children's' images to begin the scanning process. The bottom of this screen may include a link request tips about ear health. The same screen may include an "Add a child" link. To add a child, the user presses the link, and the application walks the user through the process to add a child. During the process of adding a child the user inputs the child's first name and date of birth. If the system determines the child is too young for the screening tool, a box will pop up informing the user to remove the child from the applications profile. The user then deletes the child's name and date of birth. When a user taps on the link associated with a particular child, that child's name and past scan dates and results per ear may be displayed.

The application may also include an account page that includes the user's account information and have a log out link.

In one iteration of the invention the smartphone application includes an instruction video 1706 that explains how to conduct the diagnostic test and how to attach the soundwave guide for the particular make and model of smartphone being used. The smartphone application may again display the make and model of smartphone being used and an alignment mark 1506 or alignment diagram appears on the smartphone screen 1708A, B, indicating where to align the alignment mark 1508 on a pop-open or other type of soundwave guide with an opening 1709 directed down or directed to the side. The user attaches the soundwave guide to his/her particular smartphone according to the instructions in the video 1706.

During the testing phase 1604, the smartphone application displays the "Run Open Air Test" screen 1710, where the user touches the words "Run Open Air Test" to initiate the test calibration signal(s). Another embodiment of the invention may use the words "Run Closed Test" on screen 1710. where the user runs a test that is a closed test by placing the soundwave guide tip against a finger and runs the test. In accordance with some aspects and embodiments of the invention, the scope of the invention is not limited by the wording use on the display, as long as the intent of the words convey the proper information to the user for taking action needed or desired.

According to various aspects and embodiments of the invention, the Closed Test is incorporated into the system to calibrate the interference from the soundwave guide itself during the examination of a patient's ear. Once the Closed Test is completed and the soundwave guide's soundwave interference is calibrated, the interference from the soundwave guide can be subtracted from a completed exam of a patient's ear. For example, during a diagnostic exam for otitis media the reflected waveform 212 that the cell phone speaker picks up will include both a reflected waveform from the eardrum and an interfering reflected waveform from the soundwave guide. Because the system has previously recorded the reflected waveform from the soundwave guide in the Open Test, the soundwave guide reflected waveform can be subtracted from the completed diagnostic exam (including both reflected waveforms) to obtain an accurate assessment of the status of the eardrum.

According to various aspects and embodiments of the invention, the calibration of the calibration process incorporating the Closed Test are:

(1) Recording with the cone at/near the ear—The recording of the ear response occurs in the same way as before with the Open-Air Test screen 1710, but an additional process is used to attempt to isolate the ear response to obtain more fidelity using the Closed Test.

(2) Determining the impulse response of the cone—A recording is made with the finger covering the hole on the cone. Using adaptive filtering techniques, a time domain impulse response is extracted. There are a few advantages of adaptive filtering are very similar to those of a longer sequence: (a) Adaptive filtering by its nature provides significant averaging; and (b) Adaptive filtering is far less susceptible to short bursts of interference; and smooth response results.

(3) Determining the impulse response of the combined cone and ear—In the same way as the measurement of the cone by itself, the impulse response of the combine signal from the cone and the inner ear is extracted.

(4) Separating the ear response from the Closed Test (finger) response—Noting that the recording process occurs at the same time as the sound excitation. The working assumption here is that the analogue/digital (ND) and D/A of the phone are run using the same clock. This means that a response from in the ear will be sampled at an aligned sample time from a fine phase point of view. However, there could be arbitrary sized buffers between the play and record, so an alignment is required to determine the impulse response accurately, since the recording begins at the same time as the excitation played, but the buffering will cause an arbitrary misalignment in time.

Also, since the cone only recording is done at a different time than the combined recording, the time delay between play and record can be different from the cone only to the cone plus inner ear. Another issue to be compensated is the levels of the two recording will also be different. These two issues will be compensated.

(5) The time alignment process—As mentioned above, the recording of the reflected waveform 212 is started when the excitation begins to play the emerging and initial acoustic waveform 210. The delay till evidence is see in the recording in the processor 102 can be an arbitrary time.

As a first step, a coarse assessment is made to find the start of the energy in the captures of the reflected waveform 212. This coarse delay estimate is compensated when starting the correlation processing between the recording and the pure reference signal, which has been sent out through the speaker. This coarse delay may still be off by a few samples from that desired, for later processing.

(6) Fine time alignment—Since the intent of the new scheme is to subtract the time domain response of the cone only capture (Closed Test) from that of the combine cone and ear response, the two signals are now checked for fine delay differences using a subtraction process. When the two are correctly aligned, the residual energy, after the subtraction, will be at a minimum compared to other possible relative delays.

(7) The scaling alignment process—In this embodiment, the gain adjustment to match the two signals is performed after the fine time alignment is complete. The estimate of gain differences is now made using a scale factor on one of the impulse responses when performing the subtraction. In a manner similar to the alignment, the minimum residual energy will occur after the subtraction when the best scale factor is found.

(8) Identifying the inner ear response—Once the alignment has been adjusted, and the best scale factor has been found, the impulse response difference is used to find the frequency response of the isolated inner ear response can be calculated using a Fast Fourier Transform (FFT), in accordance with the various aspects and embodiments of the invention. This response should have all the advantages mention with respect to smoother responses, averaging and noise rejection, and inner ear signal isolation.

(9) Alleviation of device equalization—As suggested above, the need for equalization should be, at least, mitigated if not eliminated, because the final frequency domain response should include only the inner ear response. Everything about the cone placement, its response, and the phone specific characteristics should have been common to both the finger on the cone and the combined cone with inner ear recordings should have been removed in the subtraction.

The user/caregiver then places the soundwave guide tip 1304A, B up to the patient's ear canal opening and is directed by the smartphone application screen to "Start Ear Scan" 1712. One embodiment of the application instructs the user to press the "Start ear scan" button and displays a three-second countdown during which the user places the soundwave guide into the opening of the patient's ear canal. In another embodiment the instructional video 1706 directs the user to first place the soundwave guide into the opening of the child's ear and then touch the "Start Ear Scan" button on the screen and the diagnostic signal begin to play. The smartphone application then displays a countdown 1714A, B, and C on the smartphone screen. After the countdown reaches "1 at 1714C the diagnostic signals begin, and the smartphone application displays a "Signal Animation Display" 1716 on the smartphone screen. If the application detects there is a problem with the smartphone being used or a user error, one embodiment of the application will show pop-up windows on the smartphone screen indicating, but not limited to: "microphone permission error," "incompatible phone" and/or "noise or movement detected." The Processing Phase 1606 now begins. After the processing phase ends the smartphone application displays the results of the diagnostic test for AOM and OME on the smartphone screen 1718. Here, the diagnostic text indicates "Middle Ear Fluid Unlikely" 1718.

Certain methods according to the various aspects of the invention may be performed by instructions that are stored upon a non-transitory computer readable medium or memory and executed by a processor. The non-transitory computer readable medium stores code including instructions that, if executed by one or more processors, would cause a system or computer to perform steps of the method described herein. The non-transitory computer readable medium includes: a rotating magnetic disk, a rotating optical disk, a flash random access memory (RAM) chip, and other mechanically moving or solid-state storage media. Any type of computer-readable medium is appropriate for storing code comprising instructions according to various example.

Certain examples have been described herein and it will be noted that different combinations of different components from different examples may be possible. Salient features are presented to better explain examples; however, it is clear that certain features may be added, modified, and/or omitted without modifying the functional aspects of these examples as described.

Some examples are one or more non-transitory computer readable media arranged to store such instructions for methods described herein. Whatever machine holds non-transitory computer readable media comprising any of the necessary code may implement an example. Some examples may be implemented as: physical devices such as semiconductor chips; hardware description language representations of the logical or functional behavior of such devices; and one or more non-transitory computer readable media arranged to store such hardware description language representations. Descriptions herein reciting principles, aspects, and embodiments encompass both structural and functional equivalents thereof. Elements described herein as coupled have an effectual relationship realizable by a direct connection or indirectly with one or more other intervening elements.

Practitioners skilled in the art will recognize many modifications and variations. The modifications and variations include any relevant combination of the disclosed features. Descriptions herein reciting principles, aspects, and embodiments encompass both structural and functional equivalents thereof. Elements described herein as "coupled" or "communicatively coupled" have an effectual relationship realizable by a direct connection or indirect connection, which uses one or more other intervening elements. Embodiments described herein as "communicating" or "in communication with" another device, module, or elements include any form of communication or link and include an effectual relationship. For example, a communication link may be established using a wired connection, wireless protocols, near-filed protocols, or RFID.

The scope of the invention, therefore, is not intended to be limited to the exemplary embodiments and aspects that are shown and described herein. Rather, the scope and spirit of the invention is embodied by the appended claims.

What is claimed is:

1. A method for directing a caregiver to properly conduct a diagnostic test for otitis media in a patient's ear using a screen display of a smartphone, the method comprising:
   accessing a diagnostic application stored on the smartphone to provide information about the smartphone to the diagnostic application;
   displaying an alignment indicator, wherein the alignment indicator includes at least one of a mark and a line, on the screen display that is aligned with an attachment indicator guide on a soundwave guide to ensure proper positioning of the soundwave guide on the smartphone;
   receiving instructions for proper placement of a small end of the soundwave guide at an ear canal opening of the patient and how to run the diagnostic test;
   generating a diagnostic signal that is sent into the patient's ear;
   analyzing a response signal that results from the diagnostic signal traveling to and back from a middle ear portion of the patient; and
   outputting a message that indicates a condition of the middle ear portion.

2. The method of claim 1, wherein the message is at least one of "Middle Ear Fluid Likely" or "Middle Ear Fluid Unlikely".

3. The method of claim 1 further comprising calibrating the smartphone to generate the diagnostic signal.

4. The method of claim 3 further comprising starting a countdown time for initiating the diagnostic test that sends the diagnostic signal into the patient's ear through the soundwave guide.

5. The method of claim 3, wherein the calibration of the smartphone is done with a machine learning model.

\* \* \* \* \*